(12) United States Patent
Curley

(10) Patent No.: US 11,918,277 B2
(45) Date of Patent: Mar. 5, 2024

(54) INFERRED MAXIMUM TEMPERATURE MONITORING FOR IRRIGATED ABLATION THERAPY

(71) Applicant: Thermedical, Inc., Waltham, MA (US)

(72) Inventor: Michael G. Curley, Weston, MA (US)

(73) Assignee: THERMEDICAL, INC., Waltham, MA (US)

( * ) Notice: Subject to any disclaimer, the term of this patent is extended or adjusted under 35 U.S.C. 154(b) by 453 days.

(21) Appl. No.: 16/035,797

(22) Filed: Jul. 16, 2018

(65) Prior Publication Data

US 2020/0015880 A1   Jan. 16, 2020

(51) Int. Cl.
| | | |
|---|---|---|
| *A61B 18/12* | (2006.01) | |
| *A61B 18/14* | (2006.01) | |
| *A61B 18/00* | (2006.01) | |

(52) U.S. Cl.
CPC ..... *A61B 18/14* (2013.01); *A61B 2018/00011* (2013.01); *A61B 2018/00023* (2013.01);
(Continued)

(58) Field of Classification Search
CPC . A61B 18/14; A61B 18/1477; A61B 18/1482; A61B 18/1492; A61B 2018/00011; A61B 2018/00023; A61B 2018/00029; A61B 2018/00035; A61B 2018/00041; A61B 2018/00577;
(Continued)

(56) References Cited

U.S. PATENT DOCUMENTS

| | | |
|---|---|---|
| 4,160,455 A | 7/1979 | Law |
| 4,424,190 A | 1/1984 | Mather, III et al. |

(Continued)

FOREIGN PATENT DOCUMENTS

| | | |
|---|---|---|
| CN | 1159154 A | 9/1997 |
| CN | 1323233 A | 11/2001 |

(Continued)

OTHER PUBLICATIONS

Brace CL. Microwave tissue ablation: biophysics, technology, and applications.; Crit Rev Biomed Eng. 2010;38(1):65-78.

(Continued)

*Primary Examiner* — Jaymi E Della
(74) *Attorney, Agent, or Firm* — Barnes & Thornburg LLP

(57) ABSTRACT

Methods and systems utilizing inferred maximum temperature monitoring for irrigated ablation therapy are described herein. In one embodiment, a method for ablating tissue includes positioning an elongate body proximate to tissue, where the elongate body includes an ablation element and at least one temperature sensor coupled thereto. The method can include simultaneously delivering ablative energy to the tissue through the ablation element and liquid through the elongate body. The method can further include pausing delivery of ablative energy and liquid, as well as sensing a temperature of the ablation element while delivery of ablative energy and liquid is paused. The method can further include any of terminating delivery of ablative energy and liquid and resuming delivery of ablative energy and liquid based on a comparison of the sensed temperature to a reference temperature.

23 Claims, 12 Drawing Sheets

(52) U.S. Cl.
CPC .......... *A61B 2018/00029* (2013.01); *A61B 2018/00035* (2013.01); *A61B 2018/00041* (2013.01); *A61B 2018/00577* (2013.01); *A61B 2018/00678* (2013.01); *A61B 2018/00702* (2013.01); *A61B 2018/00714* (2013.01); *A61B 2018/00744* (2013.01); *A61B 2018/00791* (2013.01); *A61B 2018/00821* (2013.01); *A61B 2218/002* (2013.01)

(58) Field of Classification Search
CPC .......... A61B 2018/00702; A61B 2018/00714; A61B 2018/00744; A61B 2018/00791; A61B 2018/00803; A61B 2018/00821; A61B 18/00–28; A61B 2018/00005–266
See application file for complete search history.

(56) References Cited

U.S. PATENT DOCUMENTS

| | | |
|---|---|---|
| 5,190,538 A | 3/1993 | Hussein et al. |
| 5,271,413 A | 12/1993 | Dalamagas et al. |
| 5,336,222 A | 8/1994 | Durgin, Jr. et al. |
| 5,403,311 A | 4/1995 | Abele et al. |
| 5,409,487 A | 4/1995 | Jalbert et al. |
| 5,431,648 A | 7/1995 | Lev |
| 5,431,649 A | 7/1995 | Mulier et al. |
| 5,437,629 A | 8/1995 | Goldrath |
| 5,437,673 A | 8/1995 | Baust et al. |
| 5,449,380 A | 9/1995 | Chin |
| 5,456,682 A | 10/1995 | Edwards et al. |
| 5,458,597 A | 10/1995 | Edwards et al. |
| 5,462,521 A | 10/1995 | Brucker et al. |
| 5,472,441 A | 12/1995 | Edwards et al. |
| 5,496,271 A | 3/1996 | Burton et al. |
| 5,522,815 A | 6/1996 | Durgin, Jr. et al. |
| 5,545,195 A | 8/1996 | Lennox et al. |
| 5,549,559 A | 8/1996 | Eshel |
| 5,573,510 A | 11/1996 | Isaacson |
| 5,609,151 A | 3/1997 | Mulier et al. |
| 5,653,692 A | 8/1997 | Masterson et al. |
| 5,697,949 A | 12/1997 | Giurtino et al. |
| 5,728,143 A | 3/1998 | Gough et al. |
| 5,735,846 A | 4/1998 | Panescu et al. |
| 5,800,482 A | 9/1998 | Pomeranz et al. |
| 5,827,269 A | 10/1998 | Saadat |
| 5,891,094 A | 4/1999 | Masterson et al. |
| 5,891,134 A | 4/1999 | Goble et al. |
| 5,944,713 A | 8/1999 | Schuman |
| 5,954,719 A | 9/1999 | Chen et al. |
| 5,964,791 A | 10/1999 | Bolmsjo |
| 6,024,743 A | 2/2000 | Edwards |
| 6,030,379 A | 2/2000 | Panescu et al. |
| 6,032,077 A | 2/2000 | Pomeranz |
| 6,033,383 A | 3/2000 | Ginsburg |
| 6,045,549 A | 4/2000 | Smethers et al. |
| 6,056,746 A | 5/2000 | Goble et al. |
| 6,071,280 A | 6/2000 | Edwards et al. |
| 6,080,151 A | 6/2000 | Swartz et al. |
| 6,090,106 A | 7/2000 | Goble et al. |
| 6,112,123 A | 8/2000 | Kelleher et al. |
| 6,119,041 A | 9/2000 | Pomeranz et al. |
| 6,139,570 A | 10/2000 | Saadat et al. |
| 6,139,571 A | 10/2000 | Fuller et al. |
| 6,179,803 B1 | 1/2001 | Edwards et al. |
| 6,208,881 B1 | 3/2001 | Champeau |
| 6,217,573 B1 * | 4/2001 | Webster ............ A61B 18/1492 606/34 |
| 6,233,490 B1 | 5/2001 | Kasevich |
| 6,235,023 B1 * | 5/2001 | Lee .................. A61N 1/06 606/41 |
| 6,238,393 B1 | 5/2001 | Mulier et al. |
| 6,272,370 B1 | 8/2001 | Gillies et al. |
| 6,302,904 B1 | 10/2001 | Wallsten et al. |
| 6,315,777 B1 | 11/2001 | Comben |
| 6,328,735 B1 | 12/2001 | Curley et al. |
| 6,337,994 B1 | 1/2002 | Stoianovici et al. |
| 6,358,273 B1 | 3/2002 | Strul et al. |
| 6,405,067 B1 | 6/2002 | Mest et al. |
| 6,409,722 B1 | 6/2002 | Hoey et al. |
| 6,411,852 B1 | 6/2002 | Danek et al. |
| 6,443,947 B1 | 9/2002 | Marko et al. |
| 6,463,332 B1 | 10/2002 | Aldrich |
| 6,464,694 B1 | 10/2002 | Massengill |
| 6,468,274 B1 | 10/2002 | Alleyne et al. |
| 6,475,213 B1 | 11/2002 | Whayne et al. |
| 6,477,396 B1 | 11/2002 | Mest et al. |
| 6,494,902 B2 | 12/2002 | Hoey et al. |
| 6,514,251 B1 | 2/2003 | Ni et al. |
| 6,529,756 B1 | 3/2003 | Phan et al. |
| 6,564,096 B2 | 5/2003 | Mest |
| 6,565,561 B1 | 5/2003 | Goble et al. |
| 6,603,997 B2 | 8/2003 | Doody |
| 6,620,155 B2 | 9/2003 | Underwood et al. |
| 6,641,580 B1 | 11/2003 | Edwards et al. |
| 6,669,685 B1 | 12/2003 | Rizoiu et al. |
| 6,678,552 B2 | 1/2004 | Pearlman |
| 6,702,810 B2 | 3/2004 | McClurken et al. |
| 6,752,802 B1 | 6/2004 | Isenberg et al. |
| 6,772,012 B2 | 8/2004 | Ricart et al. |
| 6,814,730 B2 | 11/2004 | Li |
| 6,904,303 B2 | 6/2005 | Phan et al. |
| 6,972,014 B2 | 12/2005 | Eum et al. |
| 7,001,378 B2 | 2/2006 | Yon et al. |
| 7,025,768 B2 | 4/2006 | Elliott |
| 7,070,597 B2 | 7/2006 | Truckai et al. |
| 7,101,369 B2 | 9/2006 | van der Welde |
| 7,160,259 B2 | 1/2007 | Tardy et al. |
| 7,179,256 B2 | 2/2007 | Mest |
| 7,207,989 B2 | 4/2007 | Pike, Jr. et al. |
| 7,244,254 B2 | 7/2007 | Brace et al. |
| 7,270,659 B2 | 9/2007 | Ricart et al. |
| 7,311,703 B2 | 12/2007 | Turovskiy et al. |
| 7,387,625 B2 | 6/2008 | Hovda et al. |
| 7,387,630 B2 | 6/2008 | Mest |
| 7,412,273 B2 | 8/2008 | Jais et al. |
| 7,416,552 B2 | 8/2008 | Paul et al. |
| 7,468,057 B2 | 12/2008 | Ponzi |
| 7,507,222 B2 | 3/2009 | Cindrich et al. |
| 7,559,905 B2 | 7/2009 | Kagosaki et al. |
| 7,604,634 B2 | 10/2009 | Hooven |
| 7,666,166 B1 | 2/2010 | Emmert et al. |
| 7,815,590 B2 | 10/2010 | Cooper |
| 7,879,030 B2 | 2/2011 | Paul et al. |
| 7,938,822 B1 | 5/2011 | Berzak et al. |
| 7,951,143 B2 | 5/2011 | Wang et al. |
| 7,993,335 B2 | 8/2011 | Rioux et al. |
| 8,128,620 B2 | 3/2012 | Wang et al. |
| 8,128,621 B2 | 3/2012 | Wang et al. |
| 8,273,082 B2 | 9/2012 | Wang et al. |
| 8,287,531 B2 | 10/2012 | Mest |
| 8,333,762 B2 | 12/2012 | Mest et al. |
| 8,369,922 B2 | 2/2013 | Paul et al. |
| 8,439,907 B2 | 5/2013 | Auth et al. |
| 8,444,638 B2 | 5/2013 | Woloszko et al. |
| 8,449,535 B2 | 5/2013 | Deno et al. |
| 8,515,560 B2 | 8/2013 | Debruyne et al. |
| 8,591,507 B2 | 11/2013 | Kramer et al. |
| 8,663,226 B2 | 3/2014 | Germain |
| 8,700,133 B2 | 4/2014 | Hann |
| 8,702,697 B2 | 4/2014 | Curley |
| 8,755,860 B2 | 6/2014 | Paul et al. |
| 8,758,349 B2 | 6/2014 | Germain et al. |
| 8,864,760 B2 | 10/2014 | Kramer et al. |
| 8,945,121 B2 | 2/2015 | Curley |
| 9,033,972 B2 | 5/2015 | Curley |
| 9,061,120 B2 | 6/2015 | Osypka et al. |
| 9,125,671 B2 | 9/2015 | Germain et al. |
| 9,138,287 B2 | 9/2015 | Curley et al. |
| 9,138,288 B2 | 9/2015 | Curley |
| 9,445,861 B2 | 9/2016 | Curley |
| 9,610,396 B2 | 4/2017 | Curley et al. |
| 9,730,748 B2 | 8/2017 | Curley |
| 9,743,984 B1 | 8/2017 | Curley et al. |

(56) References Cited

U.S. PATENT DOCUMENTS

| | | |
|---|---|---|
| 9,877,768 B2 | 1/2018 | Curley et al. |
| 9,937,000 B2 | 4/2018 | Curley |
| 10,022,176 B2 | 7/2018 | Curley |
| 10,058,385 B2 | 8/2018 | Curley |
| 10,307,201 B2 | 6/2019 | Curley |
| 10,448,987 B2 | 10/2019 | Curley |
| 10,463,425 B2 | 11/2019 | Hoitink et al. |
| 10,548,654 B2 | 2/2020 | Curley |
| 10,881,443 B2 | 1/2021 | Curley |
| 11,013,555 B2 | 5/2021 | Curley et al. |
| 11,083,871 B2 | 8/2021 | Curley et al. |
| 11,135,000 B2 | 10/2021 | Curley |
| 11,583,330 B2 | 2/2023 | Curley |
| 2001/0031946 A1 | 10/2001 | Walker et al. |
| 2002/0026210 A1 | 2/2002 | Abdel-Gawwad |
| 2002/0120259 A1 | 8/2002 | Lettice et al. |
| 2002/0123749 A1 | 9/2002 | Jain |
| 2002/0153046 A1 | 10/2002 | Dantsker et al. |
| 2002/0183735 A1 | 12/2002 | Edwards et al. |
| 2003/0060862 A1 | 3/2003 | Goble et al. |
| 2003/0109871 A1 | 6/2003 | Johnson et al. |
| 2003/0120271 A1 | 6/2003 | Burnside et al. |
| 2003/0167056 A1 | 9/2003 | Jahns et al. |
| 2004/0006336 A1 | 1/2004 | Swanson |
| 2004/0116922 A1 | 6/2004 | Hovda et al. |
| 2004/0133154 A1 | 7/2004 | Flaherty et al. |
| 2004/0220559 A1 | 11/2004 | Kramer et al. |
| 2004/0230190 A1 | 11/2004 | Dahla et al. |
| 2004/0260282 A1 | 12/2004 | Gough et al. |
| 2005/0015081 A1 | 1/2005 | Turovskiy et al. |
| 2005/0055019 A1 | 3/2005 | Skarda |
| 2005/0059963 A1 | 3/2005 | Phan et al. |
| 2005/0080410 A1 | 4/2005 | Rioux et al. |
| 2005/0090729 A1 | 4/2005 | Solis et al. |
| 2005/0165391 A1 | 7/2005 | Maguire et al. |
| 2005/0187543 A1 | 8/2005 | Underwood et al. |
| 2005/0187599 A1 | 8/2005 | Sharkey et al. |
| 2005/0192652 A1 | 9/2005 | Cioanta et al. |
| 2005/0245923 A1 | 11/2005 | Christopherson et al. |
| 2005/0267552 A1 | 12/2005 | Conquergood et al. |
| 2006/0085054 A1 | 4/2006 | Zikorus et al. |
| 2006/0118127 A1 | 6/2006 | Chinn |
| 2006/0129091 A1 | 6/2006 | Bonnette et al. |
| 2006/0216275 A1 | 9/2006 | Mon |
| 2006/0241366 A1 | 10/2006 | Falwell et al. |
| 2006/0253183 A1 | 11/2006 | Thagalingam et al. |
| 2006/0259024 A1 | 11/2006 | Turovskiy et al. |
| 2006/0276780 A1 | 12/2006 | Brace et al. |
| 2006/0287650 A1 | 12/2006 | Cao et al. |
| 2007/0027448 A1 | 2/2007 | Paul et al. |
| 2007/0032786 A1 | 2/2007 | Francischelli |
| 2007/0167775 A1 | 7/2007 | Kochavi et al. |
| 2007/0185483 A1 | 8/2007 | Butty et al. |
| 2007/0219434 A1 | 9/2007 | Abreu |
| 2007/0250053 A1 | 10/2007 | Fernald et al. |
| 2007/0250056 A1 | 10/2007 | Vanney |
| 2007/0287998 A1 | 12/2007 | Sharareh et al. |
| 2007/0288075 A1 | 12/2007 | Dowlatshahi |
| 2008/0086073 A1 | 4/2008 | McDaniel |
| 2008/0154258 A1 | 6/2008 | Chang et al. |
| 2008/0161788 A1 | 7/2008 | Dando et al. |
| 2008/0161793 A1* | 7/2008 | Wang ............ A61B 18/1492 606/41 |
| 2008/0161797 A1 | 7/2008 | Wang et al. |
| 2008/0167650 A1 | 7/2008 | Joshi et al. |
| 2008/0249463 A1 | 10/2008 | Pappone et al. |
| 2008/0275438 A1 | 11/2008 | Gadsby et al. |
| 2008/0275440 A1 | 11/2008 | Kratoska et al. |
| 2008/0281200 A1 | 11/2008 | Voic et al. |
| 2008/0288038 A1 | 11/2008 | Paul et al. |
| 2008/0294096 A1* | 11/2008 | Uber, III ............ A61M 31/005 604/66 |
| 2009/0069808 A1 | 3/2009 | Pike, Jr. et al. |
| 2009/0082837 A1 | 3/2009 | Gellman et al. |
| 2009/0093811 A1 | 4/2009 | Koblish et al. |
| 2009/0118725 A1 | 5/2009 | Auth et al. |
| 2009/0118727 A1 | 5/2009 | Pearson et al. |
| 2009/0163836 A1 | 6/2009 | Sliwa |
| 2009/0192507 A1 | 7/2009 | Luttich |
| 2009/0254083 A1 | 10/2009 | Wallace et al. |
| 2010/0030098 A1 | 2/2010 | Fojtik |
| 2010/0048989 A1 | 2/2010 | Akahane |
| 2010/0094272 A1 | 4/2010 | Rossetto et al. |
| 2010/0198056 A1 | 8/2010 | Fabro et al. |
| 2010/0292766 A1 | 11/2010 | Duong et al. |
| 2010/0324471 A1 | 12/2010 | Flaherty et al. |
| 2011/0060349 A1 | 3/2011 | Cheng et al. |
| 2011/0137150 A1 | 6/2011 | Connor et al. |
| 2011/0160726 A1 | 6/2011 | Ingle |
| 2011/0184403 A1 | 7/2011 | Brannan |
| 2011/0190756 A1 | 8/2011 | Venkatachalam et al. |
| 2011/0230799 A1 | 9/2011 | Christian et al. |
| 2011/0251615 A1 | 10/2011 | Truckai et al. |
| 2011/0270246 A1 | 11/2011 | Clark et al. |
| 2011/0282342 A1 | 11/2011 | Leo et al. |
| 2012/0108938 A1 | 5/2012 | Kauphusman et al. |
| 2012/0130381 A1 | 5/2012 | Germain |
| 2012/0165812 A1 | 6/2012 | Christian |
| 2012/0253188 A1 | 10/2012 | Holland |
| 2012/0265190 A1 | 10/2012 | Curley et al. |
| 2012/0265199 A1 | 10/2012 | Curley |
| 2012/0265200 A1* | 10/2012 | Curley .............. A61B 18/04 606/41 |
| 2012/0265276 A1* | 10/2012 | Curley .............. A61B 18/04 607/98 |
| 2012/0277737 A1* | 11/2012 | Curley .............. A61B 18/16 606/33 |
| 2012/0310230 A1 | 12/2012 | Willis |
| 2013/0345670 A1* | 12/2013 | Rajagopalan ...... A61B 18/1492 604/506 |
| 2014/0052117 A1 | 2/2014 | Curley |
| 2014/0058386 A1 | 2/2014 | Clark et al. |
| 2014/0155883 A1 | 6/2014 | Marion |
| 2014/0188106 A1 | 7/2014 | Curley |
| 2014/0275977 A1 | 9/2014 | Curley et al. |
| 2014/0276743 A1 | 9/2014 | Curley |
| 2014/0276758 A1 | 9/2014 | Lawrence et al. |
| 2014/0303619 A1 | 10/2014 | Pappone et al. |
| 2014/0350542 A1 | 11/2014 | Kramer et al. |
| 2015/0066025 A1 | 3/2015 | Curley |
| 2015/0126995 A1 | 5/2015 | Govari et al. |
| 2015/0223882 A1 | 8/2015 | Curley |
| 2015/0265344 A1 | 9/2015 | Aktas et al. |
| 2015/0297290 A1 | 10/2015 | Beeckler et al. |
| 2015/0351823 A1 | 12/2015 | Curley |
| 2015/0359582 A1 | 12/2015 | Curley et al. |
| 2016/0278856 A1* | 9/2016 | Panescu ............ A61B 5/150954 |
| 2016/0354138 A1 | 12/2016 | Curley |
| 2017/0007324 A1 | 1/2017 | Kadamus et al. |
| 2017/0072193 A1 | 3/2017 | Heller et al. |
| 2017/0100582 A1 | 4/2017 | McEvoy et al. |
| 2017/0143401 A1 | 5/2017 | Woloszko et al. |
| 2017/0238993 A1 | 8/2017 | Curley |
| 2017/0296739 A1 | 10/2017 | Curley et al. |
| 2017/0333107 A1 | 11/2017 | Curley |
| 2018/0042669 A1 | 2/2018 | Curley et al. |
| 2018/0140345 A1 | 5/2018 | Curley et al. |
| 2018/0185083 A1 | 7/2018 | Curley |
| 2019/0290349 A1 | 9/2019 | Curley |
| 2019/0336729 A1 | 11/2019 | Curley et al. |
| 2020/0113614 A1 | 4/2020 | Curley |
| 2020/0138502 A1 | 5/2020 | Curley |
| 2021/0393322 A1 | 12/2021 | Curley et al. |
| 2022/0032007 A1 | 2/2022 | Curley et al. |
| 2022/0047318 A1 | 2/2022 | Curley |

FOREIGN PATENT DOCUMENTS

| | | |
|---|---|---|
| CN | 1341462 A | 3/2002 |
| CN | 1119127 C | 8/2003 |
| CN | 1456400 A | 11/2003 |
| CN | 1525839 A | 9/2004 |
| CN | 1897885 A | 1/2007 |

(56) References Cited

FOREIGN PATENT DOCUMENTS

| | | |
|---|---|---|
| CN | 1942145 A | 4/2007 |
| CN | 2885157 Y | 4/2007 |
| CN | 101115527 A | 1/2008 |
| CN | 101209217 A | 7/2008 |
| CN | 101411645 A | 4/2009 |
| CN | 101578073 A | 11/2009 |
| CN | 101653375 A | 2/2010 |
| CN | 101773699 A | 7/2010 |
| CN | 101801445 A | 8/2010 |
| CN | 201642316 U | 11/2010 |
| CN | 101999931 A | 4/2011 |
| CN | 105030325 A | 11/2015 |
| CN | 103930153 B | 9/2016 |
| CN | 103764056 B | 2/2017 |
| CN | 103619275 B | 8/2017 |
| CN | 104869929 B | 11/2018 |
| CN | 103619276 B | 7/2023 |
| EP | 0 823 843 A1 | 2/1998 |
| EP | 0 895 756 A1 | 2/1999 |
| EP | 1 033 107 A1 | 9/2000 |
| EP | 1 159 036 A1 | 12/2001 |
| EP | 0 908 156 B1 | 11/2003 |
| EP | 2 042 112 A2 | 4/2009 |
| EP | 2 430 996 A2 | 3/2012 |
| EP | 1772109 B1 | 4/2015 |
| EP | 2207492 B1 | 3/2018 |
| JP | 62-211057 A | 9/1987 |
| JP | 01-146539 A | 6/1989 |
| JP | 05-212048 A | 8/1993 |
| JP | 10-505268 A | 5/1998 |
| JP | 11-178787 A | 7/1999 |
| JP | 2003-528684 A | 9/2003 |
| JP | 2004024331 A | 1/2004 |
| JP | 2004275594 A | 10/2004 |
| JP | 2008-534081 A | 8/2008 |
| JP | 2009-504327 A | 2/2009 |
| JP | 2010505596 A | 2/2010 |
| JP | 2011-229920 A | 11/2011 |
| JP | 2014-516622 A | 7/2014 |
| JP | 2014516625 A | 7/2014 |
| JP | 2016209582 A | 12/2016 |
| JP | 62-097971 B2 | 3/2018 |
| KR | 20140022887 A | 2/2014 |
| WO | 1994010948 A1 | 5/1994 |
| WO | 96/07360 A1 | 3/1996 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 1998033428 A2 | 8/1998 |
| WO | 99/20191 A1 | 4/1999 |
| WO | 99/32186 A1 | 7/1999 |
| WO | 02/089686 A1 | 11/2002 |
| WO | 03/028524 A3 | 10/2003 |
| WO | 03/096871 A2 | 11/2003 |
| WO | 2005/048858 A1 | 6/2005 |
| WO | 2005/089663 A1 | 9/2005 |
| WO | 2006/031541 A1 | 3/2006 |
| WO | 2006/055658 A1 | 5/2006 |
| WO | 2006/071058 A1 | 7/2006 |
| WO | 2006/095171 A1 | 9/2006 |
| WO | 2006/102471 A2 | 9/2006 |
| WO | 2006/103951 A1 | 10/2006 |
| WO | 2007/080578 A2 | 7/2007 |
| WO | 2010/002733 A1 | 1/2010 |
| WO | 2010/151619 A2 | 12/2010 |
| WO | 2012/071058 A1 | 5/2012 |

OTHER PUBLICATIONS

Chinese Office Action for Application No. 201280028609.9, dated May 27, 2015. (22 pages).
Chinese Office Action for Application No. 201280028611.6, dated Jul. 29, 2015 (23 pages).
Chinese Office Action for Application No. 201280028612.0, dated Nov. 2, 2016. (8 pages).
Chinese Office Action for Application No. 201710537279.0, dated Apr. 3, 2019. (16 pages).
Chinese Office Action for Application No. 201280028621.X, dated Jul. 31, 2015. (18 pages).
Chinese Office Action for Application No. 201380053690.0, dated Sep. 30, 2016. (17 pages).
Chinese Office Action for Application No. 201380053690.0, dated Jul. 20, 2017. (18 pages).
Chinese Office Action for Application No. 2016112115279.0, dated Feb. 28, 2019. (25 pages).
Extended Search Report and Written Opinion for EP 12770537.4 dated Oct. 10, 2014 (6 pages).
Extended Search Report and Written Opinion for EP 12770631.5 dated Oct. 1, 2014 .
Extended Search Report and Written Opinion for EP 12771331.1 dated Sep. 25, 2014.
Extended European Search Report and Written Opinion for Application No. 12771601.7 dated Oct. 27, 2014 (7 pages).
European Office Action for Application No. 12771601.7, dated Jun. 13, 2018 (5 pages).
Extended Search Report and Written Opinion for EP 12771876.5 dated Oct. 13, 2014 (6 pages).
European Office Action for Application No. EP 12771876.5, dated May 31, 2018 (6 pages).
Extended European Search Report and Search Opinion for Application No. 13829821.1 dated Mar. 17, 2016 (7 pages).
Extended European Search Report and Search Opinion for Application No. 19151775.4 dated May 21, 2019 (8 pages).
International Search Report and Written Opinion for Application No. PCT/US2012/033203, dated Sep. 21, 2012. (23 pages).
International Search Report and Written Opinion for Application No. PCT/US2012/033213, dated Sep. 21, 2012. (17 pages).
International Search Report and Written Opinion for Application No. PCT/US2012/033216, dated Sep. 21, 2012. (17 pages).
International Search Report and Written Opinion for Application No. PCT/US2012/033327, dated Sep. 21, 2012. (14 pages).
International Search Report and Written Opinion for Application No. PCT/US2012/033332, dated Sep. 21, 2012. (20 pages).
International Search Report and Written Opinion for Application No. PCT/US2013/053977, dated Nov. 14, 2013. (20 pages).
International Search Report and Written Opinion for Application No. PCT/US2014/024731, dated Jul. 21, 2014 (39 pages).
International Invitation to Pay Additional Fees for Application No. PCT/US2017/044706, dated Oct. 5, 2017 (2 Pages).
International Search Report and Written Opinion for Application No. PCT/US2017/044706, dated Nov. 29, 2017 (25 pages).
Japanese Office Action for Application No. 2014-505263, dated Jan. 26, 2016 (4 pages).
Japanese Office Action for Application No. 2014-505266, dated Feb. 23, 2016 (7 pages).
Japanese Office Action for Application No. 2017-151156, dated Aug. 7, 2018 (11 pages).
Japanese Office Action for Application No. 2017-151156, dated Apr. 16, 2019 (23 pages).
Japanese Office Action for Application No. 2017-207454, dated Oct. 2, 2018 (6 pages).
Japanese Office Action for Application No. 2018-029767, dated Sep. 4, 2018 (5 pages).
David R. Lide (ed)., CRC Handbook of Chemistry and Physics, 87th Edition. 2006. p. 8-81. CRC Press, Florida.
Nath et al., Prog. Card. Dis. 37(4):185-204 (1995).
Rolf Sander, Compilation of Henry's Law Constants for Inorganic and Organic Species of Potential Importance in Environmental Chemistry. Max-Planck Institute of Chemistry. 1999, Mainz Germany. Www.henrys-law.org.
Sapareto et al., Int. J Rad. One. Biol. Phys. 10(6):787-800 (1984).
Young, S.T., et al., An instrument using variation of resistance to aid in needle tip insertion in epidural block in monkeys. Med Instrum. Oct. 1987;21(5):266-8. Abstract Only.
Chinese Office Action for Application No. 201280028620.5, dated May 27, 2015 (26 pages).

(56) References Cited

OTHER PUBLICATIONS

Chinese Office Action for Application No. 201611215279.0, dated Aug. 12, 2019 (21 pages).
International Search Report and Written Opinion for Application No. PCT/US19/30645, dated Jul. 22, 2019 (14 pages).
U.S. Appl. No. 16/673,305, filed Nov. 4, 2019, Systems and Methods for Visulaizing Fluid Enhanced Ablation Therapy.
U.S. Appl. No. 16/660,212, filed Oct. 22, 2019, Methods and Devices for Controlling Ablation Therapy.
European Invitation to Attend Oral Proceedings for Application No. 12771601.7 issued Feb. 19, 2020 (7 Pages).
Anselmino et al., "Silent Cerebral Embolism during Atrial Fibrillation Ablation: Pathophysiology, Prevention and Management," J Air Fibrillation. Aug. 31, 2013. 6(2):796.
Calkins et al., Document Reviewers: 2017 "HRS/EHRA/ECAS/APHRS/SOLAECE expert consensus statement on catheter and surgical ablation of atrial fibrillation," Europace. Jan. 1, 2018. 20(1):e1-e160.
Dello Russo et al., "Role of Intracardiac echocardiography in Atrial Fibrillation Ablation," J Atr Fibrillation. Apr. 6, 2013. 5(6):786.
Extended European Search Report for Application No. 20184347.1 dated Feb. 1, 2021 (8 pages).
Goya et al., "The use of intracardiac echocardiography catheters in endocardial ablation of cardiac arrhythmia: Meta-analysis of efficiency, effectiveness, and safety outcomes," J Cardiovasc Electrophysiol. Mar. 2020. 31(3):664-673.
Haines et al., "Microembolism and Catheter Ablation I A Comparison of Irrigated Radiofrequency and Multielectrode-phased Radiofrequency Catheter Ablation of Pulmonary Vein Ostia," Circ Arrhythm Electrophysiol. 2013. 6:16-22.
Haines et al., "Microembolism and Catheter Ablation II Effects of Cerebral Microemboli Injection in a Canine Model," Circ Arrhythm Electrophysiol. 2012. 6:23-30.
Haines, "Asymptomatic Cerebral Embolism and Atrial Fibrillation Ablation. What Price Victory?" Circ Arrhythm Electrophysiol. 2013. 6:455-457.
Hijazi et al., "Intracardiac echocardiography during interventional and electrophysiological cardiac catheterization.," Circulation. Feb. 3, 2009. 119(4):587-96.
Japanese Office Action for Application No. 2019-507789, dated Jun. 29, 2021 (13 pages).
Jongbloed et al., "Clinical applications of intracardiac echocardiography in interventional procedures," Heart. Jul. 2005. 91(7):981-90.
Kalman et al., "Biophysical characteristics of radiofrequency lesion formation in vivo: Dynamics of catheter tip-tissue contact evaluated by intracardiac echocardiography," American Heart Journal, vol. 133, Issue 1, 1997, pp. 8-18.

Marrouche et al., "Phased-array intracardiac echocardiography monitoring during pulmonary vein isolation in patients with atrial fibrillation: impact on outcome and complications," Circulation. Jun. 3, 2003. 107(21):2710-6.
Oh et al., "Avoiding microbubbles formation during radiofrequency left atrial ablation versus continuous microbubbles formation and standard radiofrequency ablation protocols: comparison of energy profiles and chronic lesion characteristics," J Cardiovasc Electrophysiol. Jan. 2006. 17(1):72-7.
Saliba et al., "Intracardiac echocardiography during catheter ablation of atrial fibrillation," Europace. 2008. 0:0-0.
Steinberg et al., "Intracranial Emboli Associated With Catheter Ablation of Atrial Fibrillation. Has the Silence Finally Been Broken?" JACC. 2011. 58(7):689-91.
Takami et al., "Effect of Left Atrial Ablation Process and Strategy on Microemboli Formation During Irrigated Radiofrequency Catheter Ablation in an In Vivo Model," Circ Arrhythm Electrophysiol. 2016. 9:e003226.
Japanese Office Action for Application No. 2019-507789, dated May 24, 2022 (11 Pages).
Extended European Search Report for Application No. 19796516.3 dated Dec. 2, 2021 (8 Pages).
Korean Office Action for Application No. 10-2019-7005130, dated Jan. 26, 2022 (13 pages).
Chinese Office Action for Application No. 201980043984.2, dated May 31, 2022. (9 pages).
Chinese Office Action for Application No. 201780062751.8, dated Jul. 1, 2022. (19 pages).
Extended European Search Report for Application No. 19837499.3 dated Apr. 8, 2022 (11 pages).
Korean Office Action for Application No. 10-2021-7023589, dated Sep. 29, 2022 (10 pages).
Chinese Search Report for Application No. 201711019074, dated Nov. 26, 2019 (2 pages).
Chinese Supplementary Search for Application No. 201711019074, dated Feb. 29, 2020 (2 pages).
Chinese First Search for Application No. 201780062751, dated Dec. 28, 2021 (1 page).
European Office Action for Application No. 19151775, dated Feb. 2, 2023 (4 pages).
Japanese Office Action for Application No. 2020-561818, dated Apr. 4, 2023 (10 pages).
Japanese Search Report for Application No. 2020-557181, dated Apr. 21, 2023 (19 pages).
Chinese Search Report for Application No. 201980047711.5, dated Oct. 28, 2023 (10 pages).

* cited by examiner

INFERRED MAXIMUM TEMPERATURE MONITORING FOR IRRIGATED ABLATION THERAPY

GOVERNMENT RIGHTS

This invention was made with government support under grant 1R44HL132746 awarded by the National Heart, Lung, and Blood Institute (NHLBI). The government has certain rights in the invention.

FIELD

This disclosure relates generally to ablation therapy and, more particularly, to inferred maximum temperature monitoring in ablation systems and methods that employ irrigation to regulate the temperature of an ablation element in contact with tissue.

BACKGROUND

The use of thermal energy to destroy bodily tissue can be applied to a variety of therapeutic procedures, including, for example, the destruction of tumors and arrhythmogenic tissue. Thermal energy can be imparted to the target tissue using various forms of energy, such as radio frequency electrical energy, microwave or light wave electromagnetic energy, or ultrasonic vibrational energy. Radio frequency (RF) ablation, for example, can be effected by placing one or more electrodes against or into tissue to be treated and passing high frequency electrical current into the tissue. The current can flow between closely spaced emitting electrodes or between an emitting electrode and a larger, common electrode located remotely from the tissue to be heated.

One disadvantage with these techniques is that maximum heating often occurs at or near the interface between the therapeutic tool and the tissue. In RF ablation, for example, the maximum heating can occur in the tissue immediately adjacent to the emitting electrode. This can reduce the conductivity of the tissue, and in some cases, can cause liquid within the tissue to boil and become vapor. As this process continues, the impedance of the tissue can increase and prevent current from entering into the surrounding tissue. Thus, conventional RF instruments can be limited in the volume of tissue that can be treated.

Irrigated ablation therapy can be used to address this shortcoming of conventional RF ablation. In irrigated ablation therapy, liquid can be circulated past the ablation element, such as the above-mentioned one or more electrodes, to prevent the above-described maximum heating at the interface between the instrument and tissue. There are a variety of forms of irrigated ablation therapy, including closed loop systems in which liquid is circulated within the instrument without being released, as well as open loop systems in which liquid is released from the instrument into surrounding tissue, blood, etc., using, e.g., one or more outlet ports formed therein. In some cases, a temperature sensor, such as a thermocouple, can be used to monitor a temperature of the ablation element directly and facilitate control of liquid irrigation rate, etc.

Regulating the temperature of the ablation element, however, can cause maximum heating to occur at a location remote from the instrument and/or ablation element itself. If such maximum heating occurs at a distance from the instrument, its ablation element, and/or its temperature sensor, the maximum temperature cannot be detected directly. This can be problematic if the therapy unknowingly creates zones of superheated tissue with liquid that approaches or exceeds 100° C. Tissue at such temperatures can be in a highly unstable state that can produce sudden and explosive conversion of liquid to vapor (e.g., steam)—an occurrence known in the field as a steam pop. Steam pops can rupture surrounding tissue and cause undesirable damage. When using irrigated ablation therapy, it can be difficult to deliver effective therapy (i.e., achieve a high enough temperature to cause desired tissue damage) while preventing the overheating that can lead to steam pops because an operator or other system control does not know the maximum temperature being reached in the tissue located a distance away from the temperature regulated (e.g., liquid-cooled) ablation element.

Prior attempts to detect tissue temperature at locations remote from an ablation instrument have focused on, e.g., positioning temperature sensors at a remote location using tines or other structures to extend the sensor away from the instrument into the surrounding tissue. Such approaches can increase the instrument's complexity and cost by introducing additional sensors, tines, extending mechanisms, etc.

Accordingly, there is a need for improved methods and systems for monitoring temperature during ablation therapy, especially maximum temperatures achieved at positions remote from an ablation instrument or ablation element, such as an RF electrode.

SUMMARY

The present disclosure is generally directed to methods and systems for monitoring temperature during ablation therapy and can infer maximum tissue temperatures achieved at locations remote from an ablation instrument having a temperature sensor coupled thereto. In contrast to prior approaches that attempt to position a temperature sensor a distance away from an ablation instrument using, e.g., tines or other extending structures, the methods and systems described herein employ a momentary pause in the delivery of ablative energy and liquid to monitor a temperature of the instrument or its ablation element. Based on whether the measured temperature increases, decreases, or stays the same during the short pause, an inference can be made regarding the temperature of tissue a distance away from the instrument, e.g., whether it is hotter, cooler, or the same temperature as tissue in contact with the instrument. As a result, methods and systems according to the teachings provided herein can monitor temperature of tissue remote from the instrument or ablation element without requiring additional temperature sensors or structures to position such sensors in the remotely-located tissue.

In one aspect, a method for ablating tissue is provided that includes positioning an elongate body proximate to tissue, where the elongate body has an ablation element and at least one temperature sensor coupled thereto. The method can further include simultaneously delivering ablative energy to the tissue through the ablation element and liquid through the elongate body, as well as pausing delivery of ablative energy and liquid, and sensing a temperature of the ablation element while delivery of ablative energy and liquid is paused. The method can further include any of terminating delivery of ablative energy and liquid, as well as resuming delivery of ablative energy and liquid based on a comparison of the sensed temperature to a reference temperature.

The methods, devices, and systems described herein can have a number of additional features and/or variations, all of which are within the scope of the present disclosure. In some embodiments, for example, the above-described positioning of the elongate body proximate to tissue can include inserting the elongate body into a tissue mass. In some such embodiments, the method can further include delivering liquid into tissue through at least one outlet port formed in the elongate body.

In other embodiments, however, positioning the elongate body proximate to tissue can include contacting tissue with a distal portion of the elongate body without penetrating the tissue. In some such embodiments, liquid delivered through the elongate body can be released through at least one outlet port formed in the elongate body. In other embodiments, liquid delivered through the elongate body can be recirculated without exiting the elongate body.

A number of actions can be taken based on the comparison of the sensed temperature to the reference temperature. For example, in some embodiments delivery of ablative energy and liquid can be terminated if the sensed temperature is greater than the reference temperature. In certain embodiments, delivery of ablative energy and liquid can be terminated if a difference between the sensed temperature and the reference temperature is greater than a threshold amount. In still other embodiments, delivery of ablative energy can be halted while delivery of liquid is resumed to continue heat convection through the tissue. Still further, in some embodiments a temperature of the liquid can be adjusted, such as to cool tissue that is overheated.

In other embodiments alternative actions can be taken. For example, in some embodiments delivery of ablative energy and liquid can be resumed if the sensed temperature and the reference temperature are substantially equal. In some embodiments, resuming delivery of ablative energy and liquid can include adjusting at least one of a power level of ablative energy, a temperature of liquid, and a flow rate of liquid. For example, in some embodiments at least one of the power level of ablative energy and the temperature of liquid can be decreased if the sensed temperature is greater than the reference temperature. In other embodiments, at least one of the power level of ablative energy and the temperature of liquid can be increased if the sensed temperature is less than the reference temperature. In still other embodiments, the flow rate of liquid can be increased if the sensed temperature is greater than the reference temperature, while in some embodiments the flow rate of liquid can be decreased if the sensed temperature is less than the reference temperature. In other words, power level and/or flow rate and/or liquid temperature can be adjusted up or down or maintained without adjustment based on a temperature detected during a pause in delivery of ablative energy and liquid.

Pausing delivery of ablative energy and liquid can be performed for any of a variety of times and at a variety of intervals to enable efficient monitoring and therapy delivery. For example, in some embodiments delivery of ablative energy and liquid can be paused for about 1 second, while in other embodiments the pause can be about 10 seconds. And in some embodiments, pausing delivery of ablative energy and liquid can occur after about 15 seconds of simultaneously delivering ablative energy and liquid. In other embodiments, however, alternative pause durations and/or intervals can be utilized, including, for example, pauses of less than about 1 second, pauses of greater than about 1 second, etc. Further, such pauses can occur after less than about 15 seconds of simultaneously delivering ablative energy and liquid in some embodiments, and after greater than about 15 seconds of simultaneously delivering ablative energy and liquid in some embodiments.

In some embodiments, the method can further include heating the liquid within the elongate body. A variety of heating temperatures can be employed. For example, in some embodiments the liquid can be heated to a temperature of about 40° C. to about 80° C. A variety of liquid flow rates can be employed as well. For example, in some embodiments a flow rate of the liquid can be up to about 20 ml/min.

A number of different ablation elements and ablative energies can be employed. For example, in some embodiments the ablation element can be an electrode and the ablative energy can be electrical energy, such as Radio Frequency (RF) electrical energy. In other embodiments, however, other sources of ablative energy can be utilized, including, for example, laser, ultrasound, microwave, resistive electrical heating, etc.

In certain embodiments, pausing delivery of ablative energy and liquid can include reversing liquid flow to counterbalance compliance pressure. Reversing liquid flow in this manner can more effectively pause delivery of ablative energy and liquid because pressure from compliance in the system can cause continued liquid flow even after stopping actuation of a pump or other liquid driver.

In other embodiments, the method can further include drawing liquid from outside the elongate body into the elongate body after pausing delivery of ablative energy and liquid. Drawing liquid back into the elongate body can increase heat transfer by utilizing convection in addition to conduction to more quickly bring a temperature sensor into equilibrium with surrounding tissue during the period when delivery of ablative energy is paused.

In another aspect, a method for ablating tissue is provided that can include positioning an elongate body proximate to tissue, where the elongate body has an ablation element and at least one temperature sensor coupled thereto. The method can further include simultaneously delivering ablative energy to the tissue through the ablation element and liquid through the elongate body for a first period of time, as well as pausing delivery of ablative energy and liquid to the tissue for a second period of time. The method can also include monitoring the temperature sensor during the second period of time, and any of terminating delivery of ablative energy and liquid, as well as resuming delivery of ablative energy and liquid at an end of the second period of time in response to a temperature profile of the temperature sensor during the second period of time.

As with the above-described aspect, a number of additional features and/or variations can be included, all of which are within the scope of the present disclosure. In some embodiments, for example, positioning the elongate body proximate to tissue can include inserting the elongate body into a tissue mass. In some embodiments, the method can further include delivering liquid into tissue through at least one outlet port in the elongate body.

In other embodiments, positioning the elongate body proximate to tissue can include contacting tissue with a distal portion of the elongate body without penetrating the tissue. In certain embodiments, liquid delivered through the elongate body can be released through at least one outlet port formed in the elongate body. In some embodiments, however, liquid delivered through the elongate body can be recirculated without exiting the elongate body.

A number of different actions can be possible in response to the temperature profile of the temperature sensor during the second period of time. In some embodiments, for example, delivery of ablative energy and liquid can be terminated if the temperature profile is increasing over the second period of time. Further, in certain embodiments delivery of ablative energy and liquid can be terminated if the temperature profile increases by at least a threshold amount over the second period of time.

Moreover, in some embodiments delivery of ablative energy and liquid can be resumed if the temperature profile is substantially constant during the second period of time. In some embodiments, resuming delivery of ablative energy and liquid can include adjusting at least one of a power level of ablative energy, a temperature of liquid, and a flow rate of liquid. For example, in certain embodiments at least one of the power level of ablative energy and the temperature of liquid can be decreased if the temperature profile is increasing over the second period of time. In some embodiments, at least one of the power level of ablative energy and the temperature of liquid can be increased if the temperature profile is decreasing over the second period of time. By way of further example, in certain embodiments the flow rate of liquid can be increased if the temperature profile is increasing over the second period of time. In some embodiments, the flow rate of liquid can be decreased if the temperature profile is decreasing over the second period of time.

The first and second periods of time can vary in different embodiments. In some embodiments, for example, the first period of time can be about 15 seconds. Further, in some embodiments the second period of time can be about 1 second. In other embodiments, however, the first period of time can be greater or less than about 15 seconds and the second period of time can be greater or less than about 1 second.

In some embodiments, the method can further include heating the liquid within the elongate body. Such heating can be accomplished using any of a variety of heating mechanisms disposed within the elongate body. Example include single- and dual-wire radio-frequency electrical heating elements, resistive electrical heating elements, ultrasonic heating elements, microwave energy heating elements, laser heating elements, etc.

Moreover, a number of different ablation elements and ablative energies can be utilized. For example, in some embodiments the ablation element can be an electrode and the ablative energy can be electrical energy, such as Radio Frequency (RF) electrical energy. In other embodiments, however, other sources of ablative energy can be utilized, including, for example, laser, ultrasound, microwave, resistive electrical heating, etc.

In certain embodiments, pausing delivery of ablative energy and liquid to the tissue can include reversing liquid flow to counterbalance compliance pressure. As noted above, reversing liquid flow in this manner can more effectively pause delivery of ablative energy and liquid because pressure from compliance in the system can cause continued liquid flow even after stopping actuation of a pump or other liquid driver.

In other embodiments, the method can further include drawing liquid from outside the elongate body into the elongate body during the second period of time. As noted above, drawing liquid back into the elongate body can increase heat transfer by utilizing convection in addition to conduction to more quickly bring a temperature sensor into equilibrium with surrounding tissue during the period when delivery of ablative energy is paused.

In another aspect, a tissue ablation system is provided that includes an elongate body having an inner lumen, an ablation element coupled to the elongate body, a temperature sensor coupled to the elongate body, a liquid source in communication with the inner lumen of the elongate body and configured to deliver liquid through the inner lumen, and a control unit. The control unit can be configured to simultaneously deliver ablative energy through the ablation element and liquid through the elongate body, to pause delivery of ablative energy and liquid, and to sense a temperature of the ablation element while delivery of ablative energy and liquid is paused. The control unit can be further configured to any of halt delivery of ablative energy and liquid, and resume delivery of ablative energy and liquid based on a comparison of the sensed temperature to a reference temperature.

As with the above-described aspects, a number of additional features and/or variations can be included, all of which are within the scope of the present disclosure. In some embodiments, for example, the elongate body can include at least one outlet port to allow liquid to flow from the inner lumen to a volume surrounding the elongate body. In certain embodiments, the elongate body can include a tissue-puncturing distal tip. Such a tip can facilitate, for example, insertion of the elongate body into a mass of tissue. In some embodiments, however, the elongate body can include a blunt distal tip. Such a tip can be used to abut against, for example, a tissue wall without penetrating into the tissue.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The aspects and embodiments of the invention described above will be more fully understood from the following detailed description taken in conjunction with the accompanying drawings, in which:

FIG. 111B is a perspective view of another embodiment of a catheter device having an elongate body for use in liquid enhanced ablation therapy;

DETAILED DESCRIPTION

Figure 1:
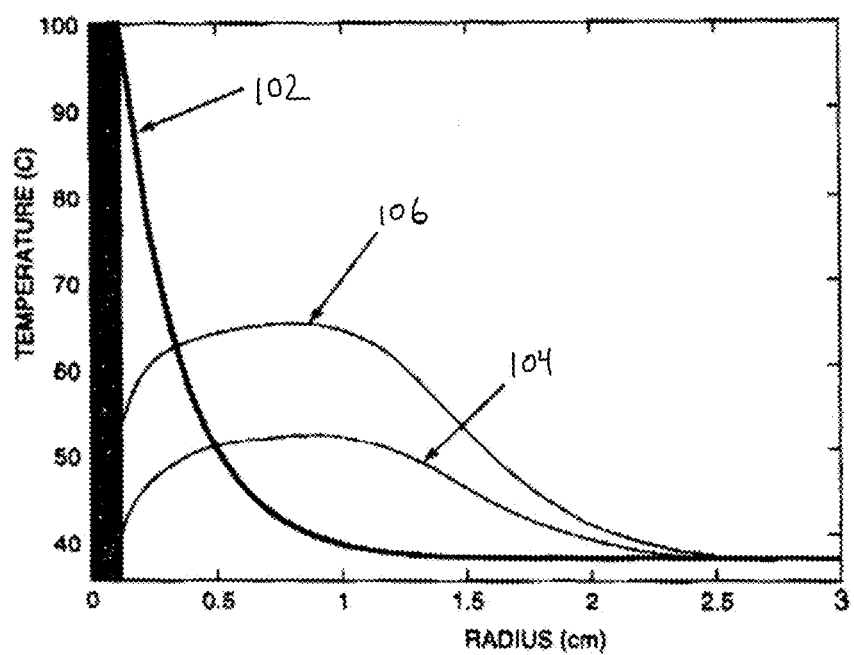
FIG. 1 is a graphical representation of simulated heating profiles for various forms of ablation.

Certain exemplary embodiments will now be described to provide an overall understanding of the principles of the structure, function, manufacture, and use of the methods and systems disclosed herein. One or more examples of these embodiments are illustrated in the accompanying drawings. Those skilled in the art will understand that the methods and systems specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

The terms "a" and "an" can be used interchangeably and are equivalent to the phrase "one or more" as utilized in the present disclosure. The terms "comprising," "having," "including," and "containing" are to be construed as open-ended terms (i.e., meaning "including, but not limited to,") unless otherwise noted. The terms "about" and "approximately" used for any numerical values or ranges indicate a suitable dimensional tolerance that allows the composition, part, or collection of elements to function for its intended purpose as described herein. Components described herein as being coupled may be directly coupled, or they may be indirectly coupled via one or more intermediate components. The recitation of any ranges of values herein is merely intended to serve as a shorthand method of referring individually to each separate value falling within the range, unless otherwise indicated herein, and each separate value is incorporated into the specification as if it were individually recited. Further, to the extent that linear or circular dimensions are used in the description of the disclosed methods and systems, such dimensions are not intended to limit the types of shapes that can be used in conjunction with such methods and systems. Equivalents to such linear and circular dimensions can be determined for any geometric shape. Further, in the present disclosure, like-numbered components of the embodiments generally have similar features. Still further, sizes and shapes of various devices, and the components thereof, can depend at least on the environment in which the devices will be used, the size and shape of components with which the devices will be used, and the methods and procedures in which the devices will be used.

All methods described herein can be performed in any suitable order unless otherwise indicated herein or otherwise clearly contradicted by context. The use of any and all examples, or exemplary language (e.g., "such as"), provided herein is intended merely to better illuminate the invention and does not impose a limitation on the scope of the invention unless otherwise claimed. No language in the specification should be construed as indicating any non-claimed element as essential to the practice of the invention. Further, to the extent the term "saline" is used in conjunction with any embodiment herein, such embodiment is not limited to use of "saline" as opposed to another liquid unless explicitly indicated. Other liquids can typically be used in a similar manner.

As noted above, the present disclosure is generally directed to methods and systems for monitoring temperature during ablation therapy and can infer maximum tissue temperatures achieved at locations remote from an ablation instrument having a temperature sensor coupled thereto. In contrast to prior approaches that attempt to position a temperature sensor a distance away from an ablation instrument using, e.g., tines or other extending structures, the methods and systems described herein employ a momentary pause in the delivery of ablative energy and liquid to monitor a temperature of the instrument or its ablation element. Based on whether the measured temperature increases, decreases, or stays the same during the short pause, an inference can be made regarding the temperature of tissue a distance away from the instrument, e.g., whether it is hotter, cooler, or the same temperature as tissue in contact with the instrument. As a result, methods and systems according to the teachings provided herein can monitor temperature of tissue remote from the instrument or ablation element without requiring additional temperature sensors or structures to position such sensors in the remotely-located tissue.

Ablation generally involves the application of high or low temperatures to cause the selective necrosis and/or removal of tissue. In the case of high temperature ablation, the delivery of therapeutic energy into tissue can cause hyperthermia in the tissue, ultimately resulting in necrosis. This temperature-induced selective destruction of tissue can be utilized to treat a variety of conditions including tumors, fibroids, cardiac dysrhythmias (e.g., ventricular tachycardia, etc.), and others. There is a known time-temperature relationship in the thermal destruction of tissue accomplished by ablation. A threshold temperature for causing irreversible thermal damage to tissue is generally accepted to be about 41° Celsius (C). It is also known that the time required to achieve a particular level of cell necrosis decreases as the treatment temperature increases further above 41° C. It is understood that the exact time/temperature relationship varies by cell type, but that there is a general relationship across many cell types that can be used to determine a desired thermal dose level. This relationship is commonly referred to as an equivalent time at 43° C. expressed as:

$$t_{eq.43°\,C.} = \int R^{(T(t)-43°)} dt \tag{1}$$

where T is the tissue temperature and R is a unit-less indicator of therapeutic efficiency in a range between 0 and 5 (typically 2 for temperatures greater than or equal to 43° C., zero for temperatures below 41° C., and 4 for temperatures between 41 and 43° C.), as described in Sapareto S. A. and W. C. Dewey, Int. J. Rad. Onc. Biol. Phys. 10(6):787-800 (1984). This equation and parameter set represents just one example of the many known methods for computing a thermal dose, and any of methodology can be employed with the methods and systems of the present disclosure. Using equation (1) above, thermal doses in the range of $t_{eq.43°\,C.}$=20 minutes to 1 hour are generally accepted as therapeutic, although there is some thought that the dose required to kill tissue is dependent on the type of tissue. Thus, therapeutic temperature may refer to any temperature in excess of 41° C., but the delivered dose and, ultimately, the therapeutic effect are determined by the temporal history of temperature (i.e., the amount of heating the tissue has previously endured), the type of tissue being heated, and equation (1). For example, Nath, S. and Haines, D. E., *Prog. Card. Dis.* 37(4):185-205 (1995) (Nath et al.) suggest a temperature of 50° C. for one minute as therapeutic, which is an equivalent time at 43° C. of 128 minutes with R=2. In addition, for maximum efficiency, the therapeutic temperature should be uniform throughout the tissue being treated so that the thermal dose is uniformly delivered.

While it can be desirable to raise tissue temperature above 41° C. to deliver effective ablation therapy, it can also be desirable to avoid overheating the tissue. For example, uninterrupted or unregulated heating of tissue can create zones of superheated tissue within a treated volume of tissue. As the temperature of tissue approaches, reaches, and exceeds 100° C., the tissue can become unstable and any liquid in the tissue (e.g., saline introduced during ablation therapy, as described below) can suddenly convert to vapor or steam—a so-called "steam pop"—that can rupture surrounding tissue and cause undesirable complications. Accordingly, ablation instruments often include a temperature sensor coupled thereto to measure temperature of the ablation element and/or tissue in contact therewith during therapy to prevent overheating.

FIG. 1 illustrates performance profiles of several ablation techniques by showing a simulated temperature achieved at a given distance from an ablation element, such as an RF electrode. The first profile 102 illustrates the performance of conventional RF ablation. As shown in the figure, the temperature of the tissue reaches a maximum value at the interface with the instrument and falls very sharply with distance from the electrode. For example, tissue at the instrument can be near 100° C. but within 10 millimeters of the ablation element the temperature of the tissue can remain at approximately body temperature (37° C.), far below the therapeutic temperatures discussed above. In addition to the risk of producing a steam pop near the ablation instrument, the high temperature tissue will more quickly desiccate, or dry up, and char. Once this happens, the impedance of the tissue rises dramatically, making it difficult to pass energy to tissue farther away from the ablation element. This limits the effective size of a treatment volume of tissue that can be created using conventional ablation techniques.

Irrigated ablation therapy can address the above-described limitations of conventional ablation techniques by passing liquid over the ablation element (e.g., RF electrode) to regulate its temperature. This can prevent overheating of the tissue in contact with the ablation instrument. For example, a second tissue temperature profile 104 is simulated based on a system similar to that described in U.S. Pat. No. 5,431,649. In this system, an electrode is inserted into tissue and imparts a 400 kHz RF current flow of about 525 mA to heat the tissue. Body temperature (37° C.) saline solution is simultaneously injected into the tissue at a rate of 10 ml/min. The resulting tissue temperature profile 104 is more uniform than profile 102 and lacks the tissue overheating present in profile 102 adjacent to the instrument.

A third tissue temperature profile 106 shows simulated results of an irrigated ablation technique utilizing heated liquid, e.g., as described in U.S. Pat. Nos. 6,328,735 and 9,138,287, the disclosures of which are hereby incorporated by reference in their entireties. In the illustrated embodiment, an electrode formed from silver/silver chloride is inserted into tissue and imparts a 480 kHz RF current flow of 525 mA to heat the tissue. Saline solution heated to 50° C. is simultaneously injected into the tissue at a rate of 10 ml/min. The resulting temperature profile 106 is both uniform and significantly above the 50° C. therapeutic threshold out to 15 millimeters from the electrode. Moreover, because the temperature is approximately uniform within this volume, the thermal dose delivered is also approximately uniform through this volume.

An important aspect of the temperature profiles 104, 106 relative to the profile 102 is that the maximum temperature of treated tissue occurs at a position remote from the ablation instrument and ablation element imparting energy to the tissue. This means that a thermocouple or other temperature sensor in contact with the ablation element or otherwise coupled to the instrument would not detect the maximum temperature of the treated volume of tissue, as it does in the case of conventional ablation therapy (e.g., profile 102).

Accordingly, it can be possible to unknowingly overheat tissue when using irrigated ablation techniques. As discussed above, tissue that is heated close to and beyond 100° C. can become superheated, unstable, and at risk of a steam pop, i.e., the explosive and sudden conversion of liquid to vapor or steam within the tissue. Due to the shape of the temperature profiles 104, 106 that reach a maximum value at a distance away from an ablation instrument and associated ablation element, a conventional temperature sensor would not detect the maximum temperature directly.

Figure 2:
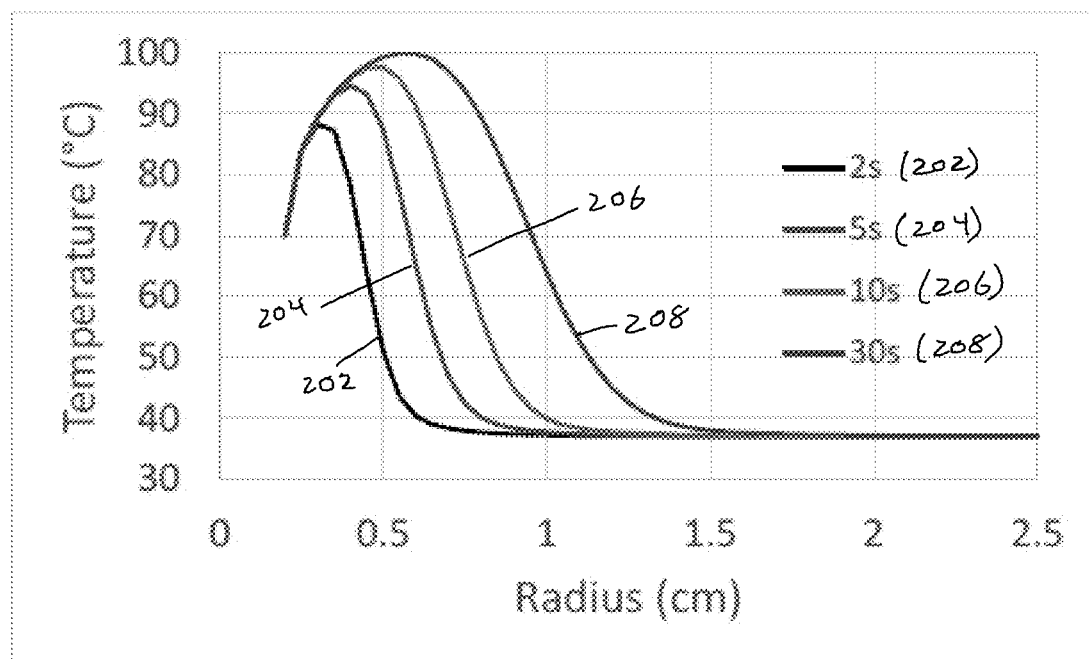
FIG. 2 a graphical representation of temperature profiles for one embodiment of irrigated ablation therapy at various time intervals.

FIG. 2 illustrates one embodiment of overheating tissue by showing simulated temperature profiles at various times after initiation of an irrigated ablation technique, e.g., a liquid enhanced ablation therapy technique using heated saline, as shown in profile 106 above. In the illustrated embodiment, therapy parameters were 62.5 W of RF power while injecting 65° C. at 10 ml/min. Profile 202 exists after 2 seconds of therapy, profile 204 after 5 seconds of therapy, profile 206 after 10 seconds of therapy, and profile 208 after 30 seconds of therapy.

A comparison of the profiles in FIG. 2 to the temperature profiles discussed above with respect to FIG. 1 can highlight the importance of administering ablation therapy using proper operating parameters (e.g., ablation element energy level, liquid temperature, liquid flow rate, treatment time, etc.). When parameters are properly selected, as in profile 106 of FIG. 1, the temperature profile in tissue can be isothermal or substantially isothermal and significantly above the therapeutic threshold throughout a desired treatment volume, e.g., out to about 15 millimeters from the electrode (other treatment distances are also possible in other embodiments). If therapy parameters are not properly configured, however, such as when a power level of ablative energy is too high relative to the flow rate and temperature of liquid being introduced into the tissue, the temperature in tissue can quickly rise away from the electrode or other ablation element. In FIG. 2, for example, the temperature profiles show a steep rise in the temperature of tissue remote from the instrument or ablation element that exceeds 90° C. within 5 seconds and approaches 100° C. about 7 mm from the instrument within 30 seconds. If treatment were continued to 60 seconds in this manner, a spherical shell between about 7 mm and about 9 mm from the instrument would exceed 100° C. and possibly result in a steam pop.

FIG. 2 also illustrates that tissue temperature close to the ablation instrument or element reaches a steady state quickly. For example, the temperature of tissue out to about 4 mm from the instrument achieves a steady state value within about 5 seconds. As therapy continues after that time, the temperature rises only in tissue beyond about 4 mm from the instrument or ablation element.

The teachings of the present disclosure utilize this characteristic of tissue in contact with and adjacent to the ablation instrument or element to detect the temperature of tissue more remote from the ablation instrument. More particularly, the methods and systems described herein momentarily pause delivery of ablative energy and liquid to tissue and monitor the temperature of tissue adjacent to the instrument by, e.g., monitoring the temperature of the ablation element itself. During such a pause, wherein further thermal energy is not being imparted to the tissue by the instrument, the tissue adjacent to the instrument will continue to rise in temperature if surrounded by hotter tissue, will begin to fall in temperature if surrounded by cooler tissue, and will remain at a constant or substantially constant temperature if surrounded by tissue of a same or substantially same temperature. Observing the temperature of tissue in contact with or closer to the ablation instrument can allow for an inference to be made about a maximum temperature achieved in tissue more remote from the instrument. This inference can help determine if the therapy is proceeding in a desired manner, e.g., similar to profile 106 in FIG. 1, or if therapy parameters are not correctly configured and are either insufficiently heating the target volume of tissue or causing tissue overheating, as in FIG. 2.

Figure 3:
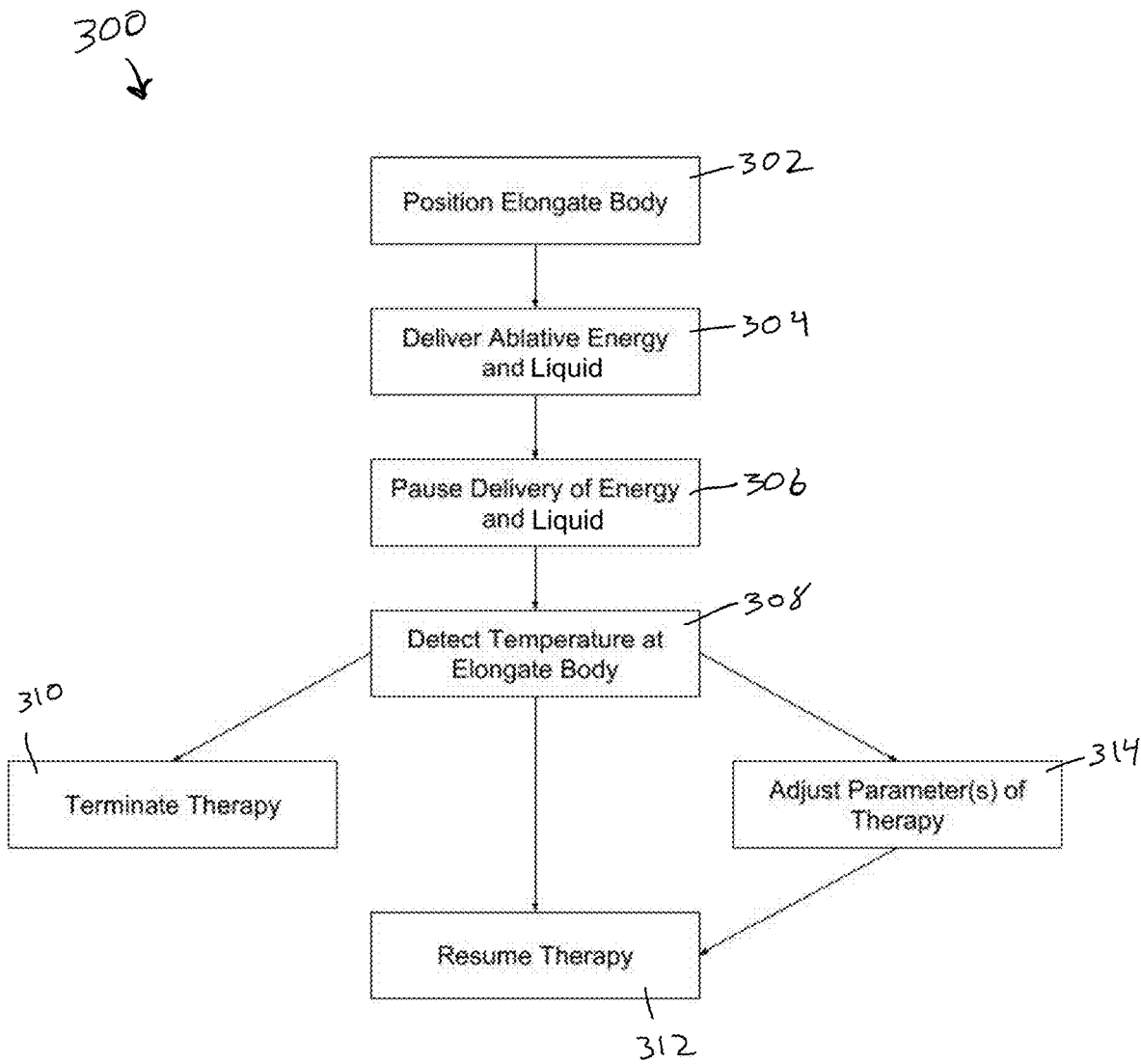
FIG. 3 is a flow chart of one embodiment of a method for inferred temperature monitoring according to the present disclosure.

FIG. 3 illustrates one embodiment of a method 300 for inferred temperature monitoring during irrigated ablation therapy. In some embodiments, the method can include positioning an elongate body or other component of an ablation instrument or device relative to tissue (302). This can include inserting the elongate body into a tissue mass in some embodiments, e.g., to position an ablation element disposed along the elongate body into the mass or volume of tissue to be treated. In other embodiments, the elongate body or other component of the ablation instrument can include a blunt distal end configured to abut against a tissue mass or wall without penetrating therethrough (e.g., a contact catheter device that can abut against a tissue wall or mass).

The method can also include delivering ablative energy and liquid (304) to cause selective necrosis or destruction of tissue. As noted above, ablative energy can be delivered in many different manners, such as radio frequency or other electrical energy, microwave or light wave electromagnetic energy (e.g., via lasers, etc.), or ultrasonic vibrational energy. Further, delivery of liquid can be accomplished in a variety of manners and can include both open and closed loop device configurations wherein liquid is either delivered from an instrument into surrounding tissue or recirculated within an instrument without being released into tissue (e.g., the liquid is delivered to a distal end of the instrument and then recirculated proximally within the instrument), respectively. Further, in some embodiments delivery of liquid can include heating the liquid, e.g., to a therapeutic temperature wherein contact with tissue can cause hyperthermia and necrosis, as described above.

The method can further include pausing delivery of ablative energy and liquid (306), e.g., after a first period of time during which energy and liquid were delivered to treat a target volume of tissue. Pausing delivery of ablative energy and liquid can effectively stop the introduction of heat into the tissue from the ablation instrument, e.g., by halting delivery of electrical or other ablative energy from any ablation element, as well as stopping the flow of liquid (e.g., heated liquid in some embodiments) into the tissue. In the case of closed loop ablation instruments, liquid recirculation within the device can be halted to prevent continued transfer of heat away from the ablation element.

Pausing delivery of ablative energy and liquid can be regulated by, e.g., a system controller or other component configured to control therapy operating parameters. Delivery of ablative energy and liquid can be paused simultaneously in certain embodiments, or delivery of either energy or liquid can be paused either before or after one another. Pausing delivery of ablative energy and liquid can be done after a first period of time during which energy and liquid are delivered. The duration of the first period of time can be set to any of a variety of values. For example, in some embodiments the first period of time can be about two seconds, about five seconds, about ten seconds, about fifteen seconds, and/or about twenty or more seconds. Moreover, the duration of the pause can also be set to any of a variety of values. For example, in some embodiments the duration of the pause can be less than a second, about one second, about two seconds, about five seconds, about ten seconds, about fifteen seconds, and/or about twenty or more seconds.

The method can also include detecting a temperature of tissue in contact with or adjacent to an ablation instrument (308). This can be accomplished using a variety of temperature sensors, such as thermocouples, etc. The temperature sensors can be coupled to the elongate body or other component of an ablation instrument in a variety of manners. For example, and as explained in more detail below, in some embodiments a thermocouple or other temperature sensor can be placed in contact with an ablation element, e.g., an RF electrode, to detect a temperature of the electrode during therapy. This temperature sensor can also be used to detect a temperature of tissue in contact with the ablation element during the pause in delivery of ablative energy from the electrode. In other embodiments, one or more temperature sensors can be disposed along the ablation instrument (e.g., along an elongate body thereof) and used to directly measure a temperature of tissue in contact therewith or indirectly measure a temperature of such tissue by measuring a temperature of a portion of the elongate body or ablation instrument in contact with the tissue (e.g., if the temperature sensor is disposed within an inner lumen of the elongate body and in contact with a sidewall thereof, etc.). Exemplary embodiments of various temperature sensors being combined with ablation instruments can be found in U.S. Pat. Pub. No. 2017/0238993, the entire contents of which is incorporated herein by reference.

Detection or sensing of temperature at the elongate body or ablation instrument can be performed at different times as well. For example, in some embodiments detecting a temperature of tissue can occur just once during the pause in delivery of ablative energy and liquid. In such embodiments, for example, the detected temperature can be compared to a reference temperature, e.g., a temperature detected during delivery of ablative energy and liquid, to determine if and how a temperature of tissue in contact with the instrument is changing during the pause in delivery of ablative energy and liquid. In other embodiments, detecting a temperature of tissue can occur at multiple times during the pause in delivery of ablative energy and liquid, e.g., every second, every two seconds, every five seconds, every 10 seconds, every 20 seconds, etc. In some embodiments, the measurement interval can be small enough, e.g., less than a second, to permit continuous or substantially continuous real-time monitoring of temperature in contact with or adjacent to the elongate body or other component of an ablation instrument. As noted above, the pause in delivery of ablative energy and liquid can have a variety of lengths. In some embodiments, the pause can be less than a second, e.g., about half a second. In other embodiments, the pause can be about a second, about two seconds, about three seconds, and/or about four or more seconds. In some embodiments, the pause in delivery of energy and liquid can last for any of about five seconds, about ten seconds, about fifteen seconds, and about twenty seconds or more. In some cases, however, pausing delivery of energy and liquid for longer periods of time to monitor temperature is not necessary to determine a temperature profile of the treated volume of tissue and can unnecessarily extend the duration of a procedure, as explained below.

Figure 4:
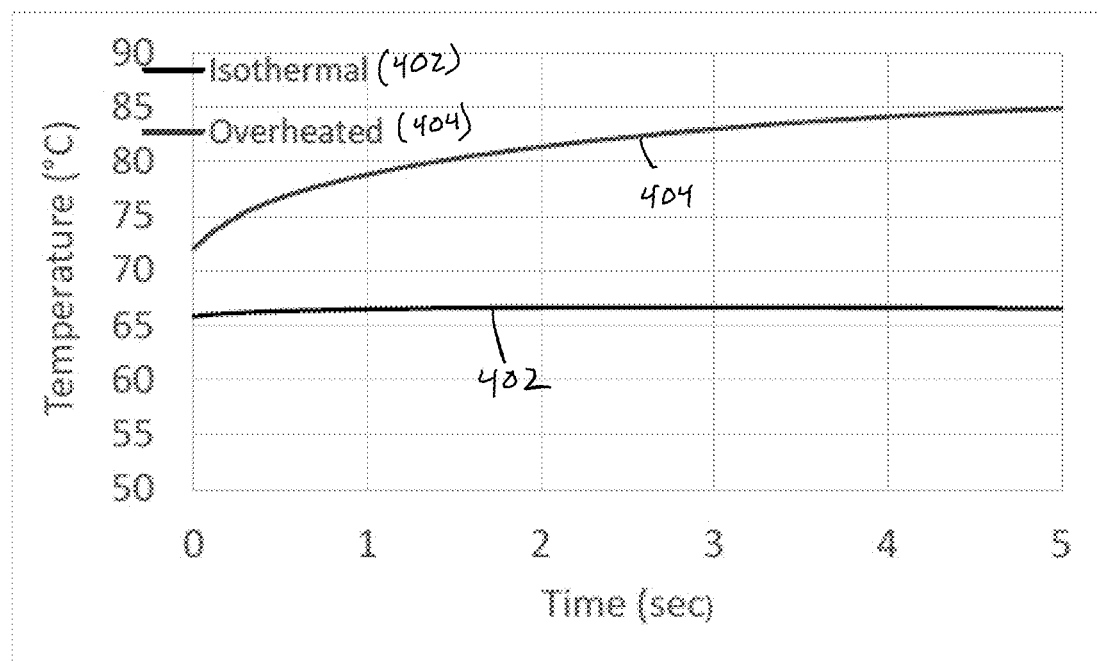
FIG. 4 is a graphical representation of temperature profiles measured following suspension of one embodiment of irrigated ablation therapy.

By comparing a reference temperature and a temperature of tissue detected during the pause in delivery of ablative energy and liquid, or by comparing multiple tissue temperatures detected over time during the pause in delivery of ablative energy and liquid, a user or system controller can determine whether to terminate therapy (310), resume therapy (312), or adjust one or more operating parameters (314) and then resume therapy. By way of example, FIG. 4 illustrates temperature response profiles for two ablation therapies during a pause in delivery of ablative energy and liquid following a period of delivery of energy and liquid (e.g., 15 seconds of active energy and liquid delivery to tissue). A first profile 402 illustrates the measured tissue temperature for an ablation therapy achieving a desired isothermal treatment volume and a second profile 404 illustrates the measured tissue temperature for an ablation therapy wherein tissue remote from the ablation element has been undesirably overheated. As shown in the figure, when therapy is paused for even as short as about 1 second, a user or the system can distinguish between a desirable isothermal profile, wherein the temperature does not change substantially, and one in which the surrounding tissue is overheated. For example, in the figure the measured temperature increases to nearly 80° C. within a second following a pause in delivery of ablative energy and liquid.

Heat transfer principles suggest that the temperature detected by the sensor in contact with, e.g., the ablation element or other portion of the instrument, rises if the surrounding tissue is hotter than the temperature at the sensor, falls if the surrounding tissue is cooler than the temperature at the sensor, and remains substantially unchanged if the surrounding tissue is at substantially the same temperature as the temperature at the sensor. The constant temperature history 402 illustrates this, as the measured temperature at the ablation element or other portion of the instrument does not meaningfully change from about 65° C. This suggests that the tissue more remote from and surrounding the temperature sensor is at about 65° C. as well. If such a temperature history is observed during a pause in delivery of energy and liquid, active delivery of ablative energy and liquid can be resumed (312) with no change in operating parameters. Alternatively, temperature profile 404 suggests that more remote tissue surrounding the tissue adjacent to the temperature sensor is overheated, as the sensed temperature rises quickly and significantly during the pause in delivery of ablative energy and liquid. This can be indicative of overheating within the target volume of tissue that could create a steam pop by, e.g., bringing a temperature of tissue surrounding the ablation instrument near to or above 100° C. If such a temperature history is observed, therapy can be terminated (310) or paused for a longer period of time to allow cooling in the target volume of tissue. In some embodiments, for example, if a difference between a detected temperature of tissue during a pause in delivery of energy and liquid and a reference temperature is greater than a threshold amount, therapy can be terminated (310). The value of the threshold amount can be set according to desired safety margins. Moreover, in some embodiments the threshold can be set as an absolute temperature rather than a difference between a measured temperature and a reference temperature, e.g., if the measured temperature rises above a certain value (e.g., 80° C. or another desired maximum temperature), therapy can be terminated.

Alternatively, one or more operating parameters of the therapy can be adjusted (314) to reduce or eliminate the overheating and achieve the desired isothermal heating profile 402. Depending on the type of irrigated ablation therapy being used, there may be a variety of parameters that can be adjusted prior to resuming delivery of energy and liquid. For example, liquid enhanced ablation, such as that described in U.S. Pat. No. 6,328,735 incorporated by reference above, can have a number of parameters that can be varied to adjust a temperature profile of tissue being treated. For example, when using such an ablation technique, an operator or control system can modify parameters such as saline temperature (e.g., from about 40° C. to about 80° C.), saline flow rate (e.g., from about 0 ml/min to about 20 ml/min), RF signal or other ablative energy power (e.g., from about 0 W to about 100 W), and duration of treatment (e.g., from about 0 minutes to about 10 minutes) to adjust the temperature profile. By way of further example, in some embodiments the power level of the ablative energy can be decreased to impart less energy into the tissue and reduce heating therein. In some embodiments, the temperature of the liquid can also or alternatively be decreased to decrease the temperature of the surrounding tissue. In other embodiments, the flow rate of the liquid can be increased to cool the tissue and/or prevent the heat from being concentrated in a single area. Of course, the converse can also be performed if the temperature profile observed during a pause in delivery of ablative energy and liquid indicates that not enough heating is occurring in the target volume of tissue. For example, if the measured temperature during the pause is less than a reference temperature during delivery of ablative energy and liquid, or if a series of temperatures measured during a pause in delivery of energy and liquid shows a downward trend, one or more of the power level of the ablative energy and the temperature of the liquid can be increased, or the flow rate of the liquid can be decreased to ensure that the surrounding tissue is appropriately heated.

Note that the method steps 304-314 can be repeated at various intervals throughout the duration of an ablation procedure to guard against undesirable tissue overheating. For example, after resuming therapy (312) ablative energy and liquid can be delivered (304) for an additional period of time, e.g., 15 seconds or some other period of time as described above, before delivery can be paused (306) again. During this additional pause, temperature can be detected (308) again and therapy either terminated, resumed under current operating parameters, or resumed under different operating parameters.

FIGS. 5A-7B illustrate profiles that depict temperature (T) relative to distance (D) from an ablation instrument 502 during delivery of ablative energy and liquid, as well as during a pause in delivery of energy and liquid. The figures illustrate three basic scenarios mentioned above: (1) insufficient heating of a target volume of tissue in FIGS. 5A and 5B, (2) overheating of a target volume of tissue in FIGS. 6A and 6B, and (3) isothermal heating of a target volume of tissue in FIGS. 7A and 7B.

Figure 5A:
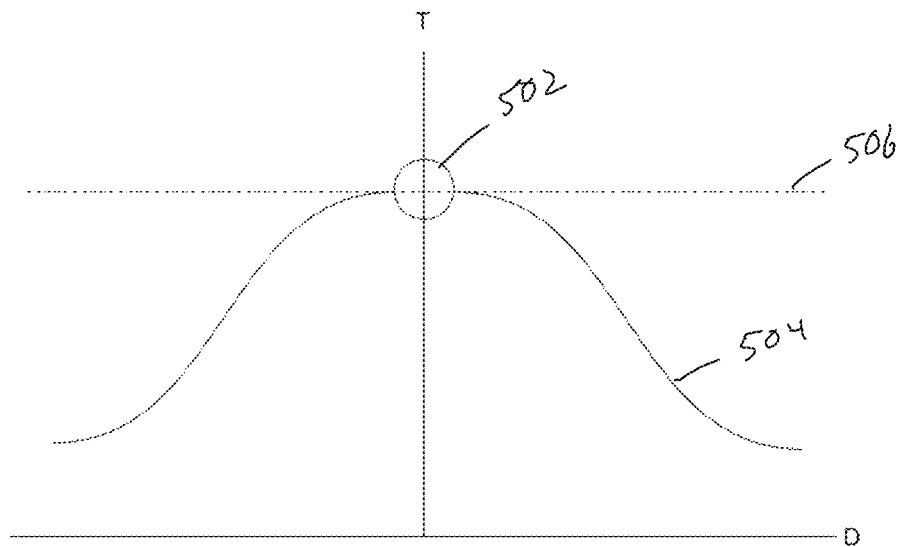
FIG. 5A is a graphical representation of a temperature profile during administration of one embodiment of irrigated ablation therapy wherein tissue remote from an ablation element is cooler than the ablation element.

Turning to FIG. 5A, the illustrated temperature profile 504 occurs during delivery of ablative energy and liquid in a first scenario wherein there is insufficient heating to bring the entirety of a target volume of tissue to or above a desired therapeutic temperature 506 (e.g., 65° C. or some other desired therapeutic temperature, as described herein). As shown in the figure, during delivery of ablative energy and liquid the temperature of tissue in contact with or immediately adjacent to the instrument 502 can reach a maximum of the desired therapeutic temperature 506 (indeed, the ablation element temperature can be regulated using irrigation to achieve this desired temperature), but the temperature of tissue more remote from the instrument can fall below the desired temperature quickly.

Figure 5B:
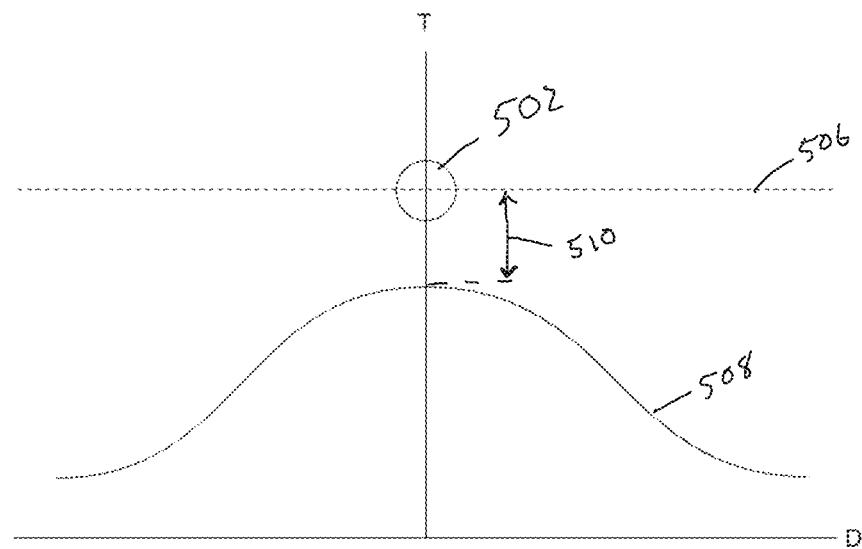
FIG. 5B is a graphical representation of the temperature profile of FIG. 5A after suspension of therapy.

After therapy is paused and no further energy is being imparted into the tissue by the instrument 502, the temperature profile 508 shown in FIG. 5B can exist. At this time, the temperature at the instrument 502 can fall below the desired therapeutic temperature 506, as shown by the temperature decrease 510. This can occur because the cooler tissue surrounding the instrument 502 can draw away heat from the tissue immediately adjacent to the instrument. If the temperature decrease 510 is observed using, e.g., a thermocouple sensing a temperature of the ablation element or another temperature sensor, therapy can be resumed to allow more time for heat to build in the target volume of tissue. Alternatively or in addition, one or more therapy parameters can be modified to impart a larger amount of energy into the tissue and achieve desired therapeutic heating of the entire targeted volume of tissue.

Figure 6A:
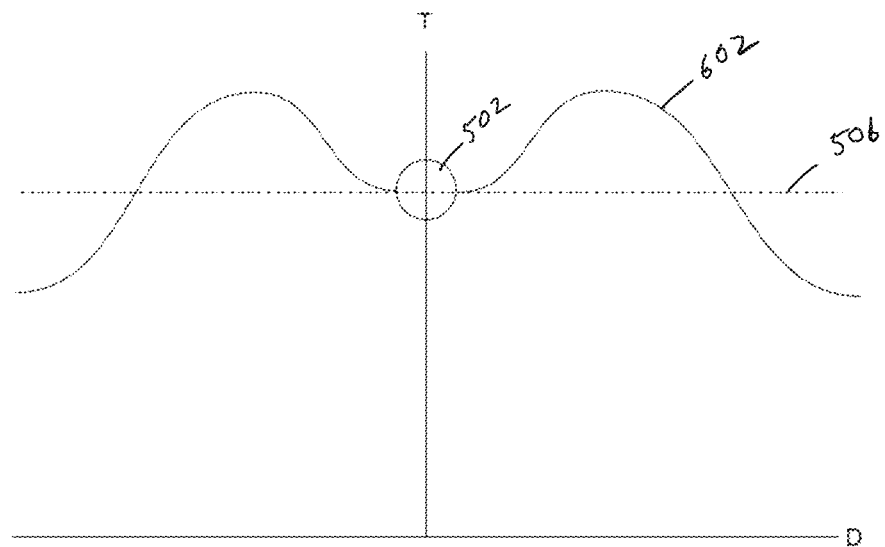
FIG. 6A is a graphical representation of a temperature profile during administration of one embodiment of irrigated ablation therapy wherein tissue remote from an ablation element is hotter than the ablation element.
Figure 6B:
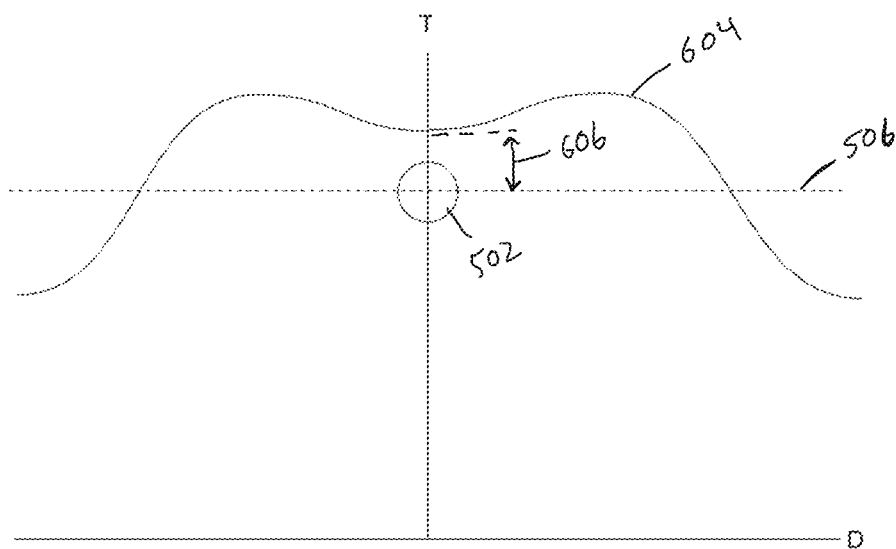
FIG. 6B is a graphical representation of the temperature profile of FIG. 6A after suspension of therapy.

FIGS. 6A and 6B illustrate a second scenario wherein the target volume of tissue experiences potentially undesirable overheating, e.g., heating that can result in the creation of a steam pop. FIG. 6A illustrates a temperature profile 602 that can exist during delivery of ablative energy and liquid in this scenario. Note that the temperature of tissue in contact with the instrument 502 or immediately adjacent thereto can be at the desired therapeutic temperature 506 because liquid irrigation can regulate the ablation element to the desired temperature. More remote from the instrument 502, however, the temperature of tissue can exceed the desired therapeutic temperature 506 and approach temperatures at or near 100° C. that can create steam pops.

FIG. 6B illustrates a temperature profile 604 in the target volume of tissue during a pause in the delivery of energy and liquid from the instrument 502. The temperature in the vicinity of the ablation element is not regulated by liquid irrigation and/or power management at this time and, as a result, the temperature will increase due to heat transfer from hotter and more remote tissue. Accordingly, the observed temperature at the instrument 502 will increase above the desired therapeutic temperature 506, as shown by the temperature increase 606. If this temperature response is observed, a user or the system can take any of the following actions: terminate therapy, pause until sufficient cooling occurs, and adjust one or more therapy parameters to provide additional cooling and/or impart less energy into the tissue to produce less heating.

Figure 7A:
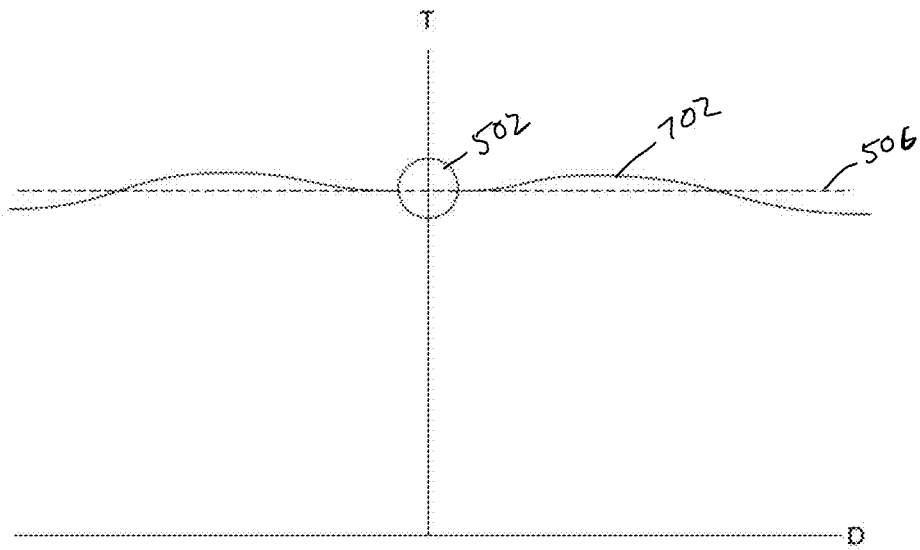
FIG. 7A is a graphical representation of a temperature profile during administration of one embodiment of irrigated ablation therapy wherein tissue remote from an ablation element is substantially the same temperature as the ablation element.
Figure 7B:
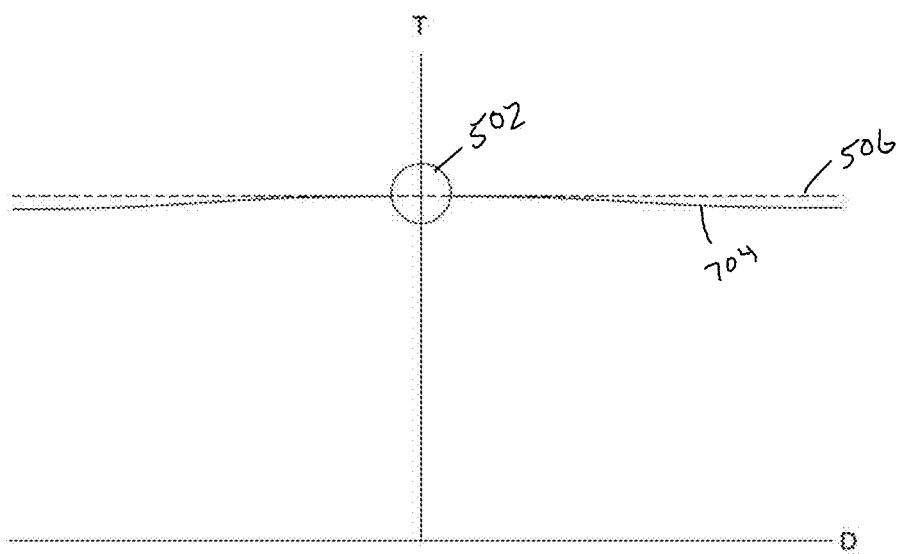
FIG. 7B is a graphical representation of the temperature profile of FIG. 7A after suspension of therapy.

FIGS. 7A and 7B illustrate a third scenario wherein a target volume of tissue experiences desired isothermal heating throughout. FIG. 7A illustrates a temperature profile 702 that can exist during delivery of ablative energy and liquid in this scenario. As in FIGS. 5A and 6A, during periods of active therapy (e.g., delivery of ablative energy and liquid), the temperature of tissue in contact with the instrument 502 or immediately adjacent thereto is regulated to the desired therapeutic temperature 506 using liquid irrigation. When therapy operating parameters are properly configured, however, a temperature of tissue throughout the targeted volume can also reach the desired therapeutic temperature 506. As shown in the figure, there can be some temperature variation due to the nature of the heating process, but the target volume of tissue can achieve substantially the desired temperature throughout without any areas of significantly over- or under-heating.

FIG. 7B illustrates a temperature profile 704 in the target volume of tissue during a pause in the delivery of energy and liquid from the instrument 502. Given that heating throughout the target volume of tissue is approximately isothermal, as shown in FIG. 7A, there is substantially no change in the temperature of tissue in contact with or adjacent to the instrument 502 during the pause as a result of heat transfer from more remote surrounding tissue. Accordingly, the temperature measured at the instrument (e.g., by measuring a temperature of the ablation element) does not change substantially. If a user or the system observes this response, delivery of ablative energy and liquid can be resumed at the current operating parameters, as desirable uniform heating is occurring.

Figure 8:
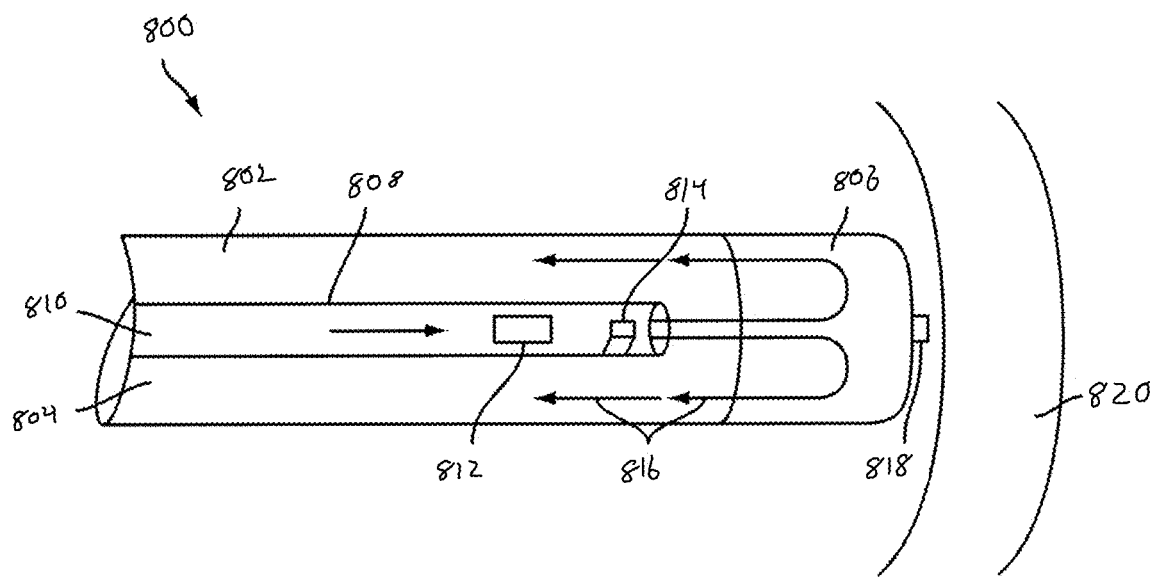
FIG. 8 is a partially-transparent side view of one embodiment of an ablation device having a closed loop flow pattern.
Figure 9:
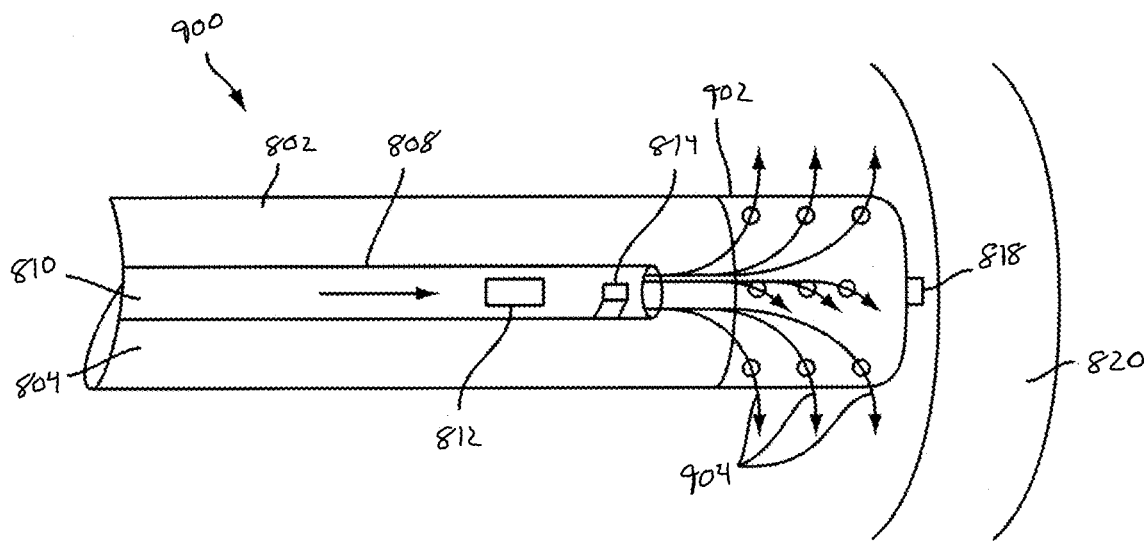
FIG. 9 is a partially-transparent side view of one embodiment of an ablation device having an open loop flow pattern.

As noted above, the methods and systems described herein can utilize a variety of types of irrigated ablation instruments that utilize liquid flow to regulate a temperature of the ablation element, including both closed and open loop liquid flow devices. In closed loop devices liquid is circulated internally without being released into tissue, while in open loop devices liquid is released from the instrument into surrounding tissue, blood, etc. FIGS. 8 and 9 illustrate exemplary embodiments of closed and open loop instruments, respectively.

Turning to FIG. 8, one embodiment of a closed loop irrigated ablation device 800 is shown. The device 800 includes an elongate body 802, which can be rigid or flexible and can be formed from a variety of biocompatible materials. For example, the elongate body 802 can be a flexible catheter body or can be a rigid body disposed at a distal end of a catheter used to introduce the elongate body 802 to a treatment site. The elongate body 802 can also include an inner lumen 804 extending therethrough that can be configured to provide a passage for liquid flow through the elongate body. Further, the particular size of the elongate body can depend on a variety of factors including the type and location of tissue to be treated, etc. By way of example only, in one embodiment, a very small elongate body can be utilized to access the heart of a patient. In such an embodiment, an appropriately sized elongate body can be, for example, a catheter having a diameter of about 8 French ("French" is a unit of measure used in the catheter industry to describe the size of a catheter and is equal to three times the diameter of the catheter in millimeters). The elongate body 802 can be formed from an electrically conductive material such that the elongate body can conduct electrical energy along its length to an ablation element 806 disposed thereon. Alternatively, the elongate body can be formed from, or coated with, an electrically insulating material and any electrical communication between any components coupled thereto can be accomplished through electrical connections running along or within the elongate body. In some embodiments, electrically insulating coatings can be combined with an elongate body formed from an electrically conductive material, e.g., wherein an electrically conductive elongate body is coated with an electrically insulating coating except for a portion of the elongate body configured to function as an ablation element.

As noted above, the elongate body 802 can include an ablation element 806 disposed along a length thereof adjacent to its distal end. As shown in the figure, in some embodiments the ablation element 806 can be positioned at the distal end of the elongate body 802. In certain embodiments, the ablation element 806 can be an electrode configured to deliver electrical energy, such as radio frequency (RF) electrical energy. In such embodiments, the ablation element 806 can be formed from a variety of materials suitable for conducting current. For example, any metal or metal salt can be used. Aside from stainless steel, exemplary metals can include platinum, gold, or silver, and exemplary metal salts can include silver/silver chloride. In one embodiment, the electrode can be formed from silver/silver chloride. One advantage of using a metal salt such as silver/silver chloride can be that it has a high exchange current density. As a result, a large amount of current can be passed through such an electrode into tissue with only a small voltage drop, thereby minimizing energy dissipation at this interface. Thus, an electrode formed from a metal salt such as silver/silver chloride can help reduce excessive energy generation at the tissue interface and thereby produce a more desirable temperature profile that requires less liquid flow to regulate.

The ablation element 806 can have a variety of shapes but, in some embodiments, can be shaped to form a blunt distal tip of the device 800. As such, the ablation element 806 can be configured to press against, or be positioned adjacent to, a tissue wall without penetrating into the tissue wall. In other embodiments, the elongate body 802 can have a pointed distal end configured for insertion into a mass of tissue and the ablation element 806 can be disposed along a length of the elongate body such that it can be positioned within the mass of tissue after the elongate body is inserted into the tissue mass (see FIG. 10).

In some embodiments, the inner lumen 804 of the elongate body 802 can include a delivery lumen 808 configured to provide a passage, e.g., through an inner lumen 810, for liquid flow from the proximal end to the distal end, and a return lumen formed by the annular space between the delivery lumen 808 and the inner wall of the inner lumen 804. The return lumen can be configured to receive liquid at a distal end thereof and deliver the liquid back to the proximal end of the elongate body 802. This allows liquid to be circulated through the elongate body without the need to release the liquid to the surrounding tissue. Similar to the elongate body 802, the delivery lumen 808 can be formed from a variety of materials that are rigid, flexible, polymeric, metallic, conductive, or insulating. Further, the delivery lumen 808 can be positioned within the inner lumen 804 of the elongate body 802, such that the delivery lumen 808 does not move with respect to the elongate body, or can be allowed to float freely within the elongate body 802. In some embodiments, the delivery lumen 808 can be a hollow tube disposed within the inner lumen of the elongate body. In addition, in certain embodiments, the return lumen can be a separate hollow tube disposed within the inner lumen 804 of the elongate body.

In some embodiments, the delivery lumen 808 can house a heating assembly or heater element 812 disposed adjacent to a distal end of the delivery lumen and configured to heat liquid flowing through the delivery lumen. The heating assembly 812 can be connected to a power supply and controller coupled to the proximal end of the elongate body 802. A number of heating assemblies can be utilized to heat liquid flowing through the delivery lumen 808, including those described in U.S. Pat. Nos. 6,328,735 and 9,138,287 incorporated by reference above. For example, the heater element 812 can be a resistive coil disposed within the delivery lumen 808. In other embodiments, however, a heating assembly 812 formed from one or more wires suspended in the delivery lumen 808 that can be used to pass RF electrical energy through the liquid flowing through the delivery lumen, thereby heating the liquid due to its inherent electrical resistivity.

In certain embodiments, the delivery lumen 808 can also house a temperature sensor 814 configured to detect the temperature of the liquid flowing through the delivery lumen 808 after it is heated by the heating assembly 812. For this reason, the temperature sensor 814 can, in some embodiments, be positioned distal to the heating assembly 812, and can be separated from the heating assembly by a distance sufficient to allow mixing of the liquid after passing through the heating assembly (e.g., about 1 mm). The temperature sensor 814 can have a variety of forms and, in some embodiments, can be a fine-wire thermocouple. The temperature sensor 814 can be connected to a controller that can utilize the detected liquid temperature to regulate the heating assembly 812.

In use, a liquid (e.g., saline) can be pumped through the delivery lumen 808 from a proximal end thereof to a distal end that is positioned adjacent to the ablation element 806. The liquid can pass by the heating assembly 812 and be heated to a desired temperature, e.g., any temperature below 100° C., or any temperature between about 40 and about 90° C., or between about 50 and about 80° C., or between about 60 and about 70° C. In some embodiments, however, cooler temperature liquids can be employed, including liquid temperatures at or below body temperature. Indeed, in some embodiments no heating assembly 812 can be present to adjust a temperature of the liquid. Moreover, in some embodiments, an additional temperature sensor (not shown) can be positioned in the delivery lumen 808 at a position proximal to the heating assembly 812 in order to determine the initial temperature of the liquid flowing through the delivery lumen 808 (and thereby determine a power output needed for the heating assembly 812). After being heated by the heating assembly 812, the liquid can mix and exit the delivery lumen 808 near the distal end of the elongate body 802 adjacent to the ablation element 806. As shown by the flow direction arrows 816, the liquid can contact an inner surface of the ablation element and subsequently be directed back toward the proximal end of the elongate body 802 through the return lumen. The movement of the liquid can transfer heat away from the ablation element 806, thereby regulating its temperature. Given a sufficient flow rate, the ablation element 806 can be regulated to about the same temperature of the liquid exiting the delivery lumen 808.

In order to confirm the effectiveness of the temperature regulation, the device 800 can also include an external temperature sensor 818 disposed on a distal end of the device 800. In some embodiments, the temperature sensor 818 can be recessed within the ablation element 806 such that it does not protrude from a distal end thereof. In still other embodiments in which the ablation element 806 is formed from a metal or other thermally conductive material, the temperature sensor 818 can be positioned inside the inner lumen 804 touching a surface of the ablation element 806. Regardless of its position, the temperature sensor 818 can be configured to detect the temperature at the interface between the ablation element 806 and a tissue surface 820. Detecting the temperature at this location can effectively measure a temperature of the tissue surface 820 and can confirm that the ablation element 806 is being cooled to the temperature of the liquid flowing from the delivery lumen 808. Furthermore, during the above-described pause in the delivery of ablative energy and liquid, the temperature sensor 818 can be utilized to detect the temperature of the ablation element and tissue in contact therewith/immediately adjacent thereto.

FIG. 9 illustrates another embodiment of an ablation device 900 having an open loop flow, as opposed to the closed loop flow shown in FIG. 8. As shown in the figure, the device 900 can include several components common to the device of FIG. 8. For example, the device 900 can include an elongate body 802 having an inner lumen 804, a delivery lumen 808 disposed within the inner lumen 804 and having its own inner lumen 810, a heating assembly 812 and temperature sensor 814 housed within the inner lumen 810, and, in some embodiments, one or more additional temperature sensors, such as the temperature sensor 818.

The device 900 differs from the device 800 in that it includes an ablation element 902 having a plurality of outlet ports or pores formed therein that communicate between an inner surface and an outer surface of the ablation element. As a result, when liquid is introduced into the inner lumen 804 adjacent to the ablation element 902, the liquid can flow through the ablation element 902 and into the body cavity or the tissue surface 820 surrounding the device 900. The resulting open-loop flow pattern is illustrated by flow direction arrows 904. As a result of the open-loop flow pattern, the device 900 can, in some embodiments, remove the separate delivery lumen 808 and simply pump liquid in a single direction through the inner lumen 804 of the elongate body 802. In such an embodiment, the heating assembly and any temperature sensors can be disposed within the inner lumen 804 of the elongate body 802.

The methods and systems described herein can also be utilized in connection with any of a variety of types of irrigated ablation therapy wherein liquid flow is used to regulate ablation element temperature to prevent overheating of tissue in contact with or immediately adjacent to the ablation element. This can include devices and systems that utilize body temperature or cooler saline or other liquid to cool an ablation element during therapy. In some embodiments, however, the teachings provided herein can be utilized in connection with liquid enhanced ablation, such as the ablation technique described in U.S. Pat. No. 6,328,735 and incorporated by reference above. Such techniques can deliver liquid heated to a therapeutic temperature into tissue along with ablative energy. FIGS. 10-13 provide additional details on exemplary embodiments of liquid enhanced ablation therapy systems and devices that can be utilized in connection with the methods described herein.

Figure 10:
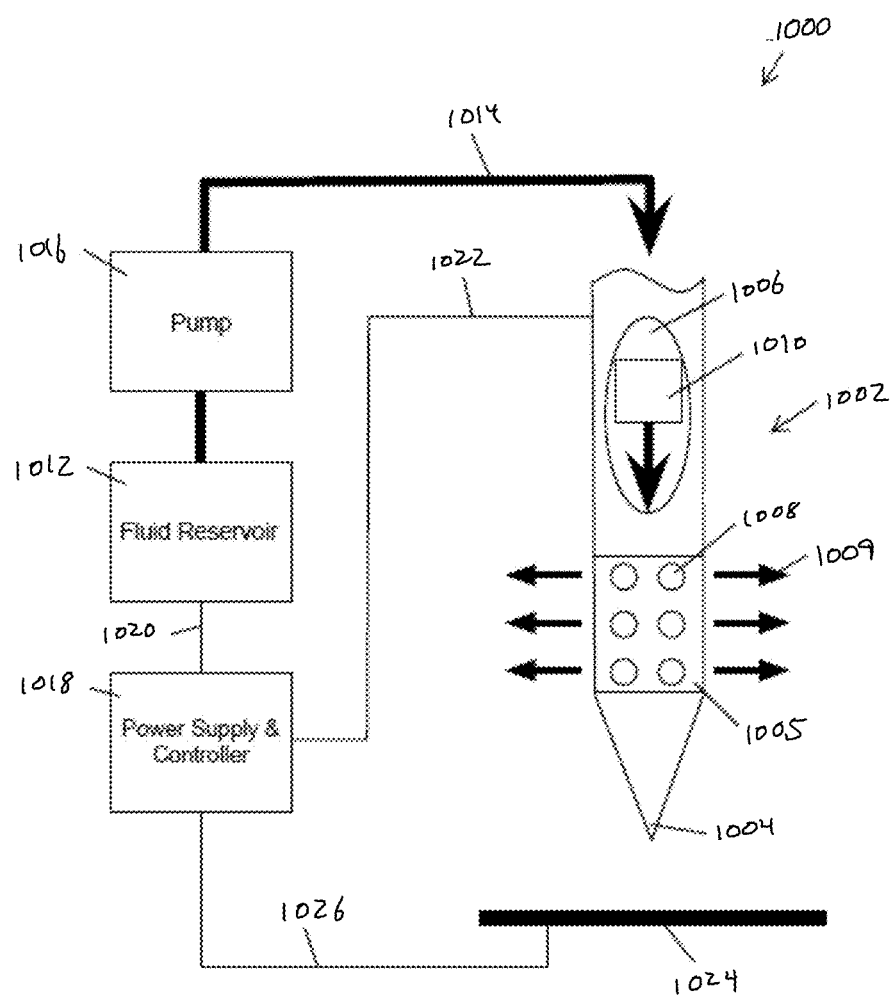
FIG. 10 is a diagram of one embodiment of a liquid enhanced ablation system.
Figure 11A:
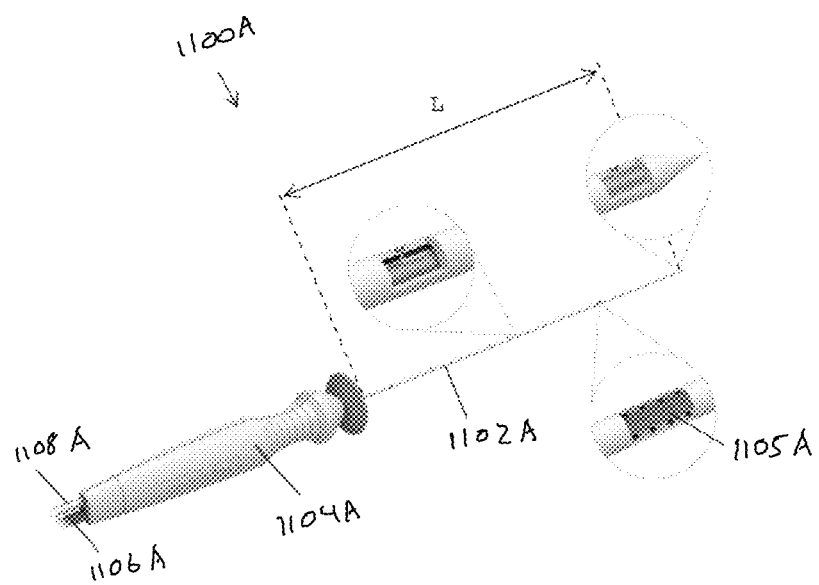
FIG. 11A is a perspective view of one embodiment of a laparoscopic device having an elongate body for use in liquid enhanced ablation therapy.

FIG. 10 illustrates a diagram of one exemplary liquid ablation system 1000. The system includes an elongate body 1002 configured for insertion into a target volume of tissue. The elongate body can have a variety of shapes and sizes according to the geometry of the target tissue. Further, the particular size of the elongate body can depend on a variety of factors including the type and location of tissue to be treated, the size of the tissue volume to be treated, etc. By way of example only, in one embodiment, the elongate body can be a thin-walled stainless steel needle between about 16- and about 18-gauge (i.e., an outer diameter of about 1.27 millimeters to about 1.65 millimeters), and having a length L (e.g., as shown in FIG. 11A) that is approximately 25 cm. The elongate body 1002 can include a pointed distal tip 1004 configured to puncture tissue to facilitate introduction of the device into a target volume of tissue, however, in other embodiments the tip can be blunt and can have various other configurations for contacting and/or abutting tissue. The elongate body 1002 can be formed from a conductive material such that the elongate body can conduct electrical energy along its length to one or more ablation elements located along a distal portion of the elongate body. Emitter electrode 1005 is an example of an ablation element capable of delivering RF energy from the elongate body.

In some embodiments, the emitter electrode 1005 can be a portion of the elongate body 1002. For example, the elongate body 1002 can be coated in an insulating material along its entire length except for the portion representing the emitter electrode 1005. More particularly, in one embodiment, the elongate body 1002 can be coated in 1.5 mil of the fluoropolymer Xylan™ 8840. The electrode 1005 can have a variety of lengths and shape configurations. In one embodiment, the electrode 1005 can be a 4 mm section of a tubular elongate body that is exposed to surrounding tissue. Further, the electrode 1005 can be located anywhere along the length of the elongate body 1005 (and there can also be more than one electrode disposed along the length of the elongate body). In one embodiment, the electrode can be located adjacent to the distal tip 1004. In other embodiments, the elongate body can be formed from an insulating material, and the electrode can be disposed around the elongate body or between portions of the elongate body. In other embodiments, the electrode can be formed from a variety of other materials suitable for conducting current. As noted above, for example, any metal or metal salt may be used.

Although the emitter electrode 1005 illustrated in FIG. 10 is configured as a continuous cylindrical band adapted for a mono-polar current flow, the electrode can also be formed in other geometries, such as spherical or helical, that form a continuous surface area, or the electrode may have a plurality of discrete portions. The electrodes may also be configured for bipolar operation, in which one electrode (or a portion of an electrode) acts as a cathode and another electrode (or portion thereof) acts as an anode.

The electrode 1005 or other ablation element can include one or more outlet ports 1008 that are configured to deliver liquid from an inner lumen 1006 extending through the elongate body 1002 into surrounding tissue (as shown by arrows 1009). Alternatively, the electrode 1005 can be positioned near one or more outlet ports 1008 formed in the elongate body 1002. In many embodiments, it can be desirable to position the electrode adjacent to the one or more outlet ports 1008 to maximize the effect of the flowing liquid on the therapy. The outlet ports 1008 can be formed in a variety of sizes, numbers, and pattern configurations. In addition, the outlet ports 1008 can be configured to direct liquid in a variety of directions with respect to the elongate body 1002. These can include the normal orientation (i.e., perpendicular to the elongate body surface) shown by arrows 1009 in FIG. 10, as well as orientations directed proximally and distally along a longitudinal axis of the elongate body 1002, including various orientations that develop a circular or spiral flow of liquid around the elongate body. Still further, in some embodiments, the elongate body 1002 can be formed with an open distal end that serves as an outlet port. By way of example, in one embodiment, twenty-four equally-spaced outlet ports 1008 having a diameter of about 0.4 mm can be created around the circumference of the electrode 1005 using Electrical Discharge Machining (EDM). In other embodiments, however, alternative manufacturing methods can be used to create the outlet ports 1008. In addition, in some embodiments, the outlet ports can be disposed along a portion of the elongate body adjacent to the electrode, rather than being disposed in the electrode itself. In still other embodiments, any of a variety of other outlet port patterns can be employed, including, for example, those described in U.S. Pat. No. 9,743,984, the entire contents of which are incorporated by reference herein.

The inner lumen 1006 that communicates with the outlet ports 1008 can also house a heating assembly 1010 configured to heat liquid as it passes through the inner lumen 1006 just prior to being introduced into tissue. Detailed discussion of various embodiments of the heating assembly 1010 suitable for use in devices and methods of the present invention can be found in related U.S. Pat. No. 9,138,287, incorporated by reference in its entirety above.

The portion of the elongate body located distal to the electrode 1005 or other ablation element can be solid or filled such that the inner lumen 1006 terminates at the distal end of the electrode 1005. In one embodiment, the inner volume of the portion of the elongate body distal to the electrode can be filled with a plastic plug that can be epoxied in place or held by an interference fit. In other embodiments, the portion of the elongate body distal to the electrode can be formed from solid metal and attached to the proximal portion of the elongate body by welding, swaging, or any other technique known in the art.

Liquid can be supplied to the inner lumen 1006 and heating assembly 1010 from a liquid reservoir 1012. The liquid reservoir 1012 can be connected to the inner lumen 1006 via a liquid conduit 1014. The liquid conduit 1014 can be, for example, a length of flexible plastic tubing. The liquid conduit 1014 can also be a rigid tube, or a combination of rigid and flexible tubing.

Liquid can be urged from the liquid reservoir 1012 into the inner lumen 1006 by a pump 1016. The pump 1016 can be a syringe-type pump that produces a fixed volume flow with advancement of a plunger (not shown). An example of such a pump is a Model 74900 sold by Cole-Palmer Corporation of Chicago, Ill. Other types of pumps, such as a diaphragm pump, may also be employed.

One type of liquid that can be used is sterile normal saline solution (defined as a salt-containing solution). However, other liquids may be used, including Ringer's solution, or concentrated saline solution. A liquid can be selected to provide the desired therapeutic and physical properties when applied to the target tissue and a sterile liquid is recommended to guard against infection of the tissue.

The pump 1016 can be controlled by a power supply and controller 1018. The power supply and controller 1018 can deliver electrical control signals to the pump 1016 to cause the pump to produce a desired flow rate of liquid. The power supply and controller 1018 can be connected to the pump 1016 via an electrical connection 1020. The power supply and controller 1018 can also be electrically connected to the elongate body 1002 via connection 1022, and to a collector electrode 1024 via connection 1026. In addition, the power supply and controller 1018 can be connected to the heating assembly 1010 through a similar electrical connection.

The collector electrode 1024 can have a variety of forms. For example, the collector electrode 1024 can be a large electrode located outside a patient's body. In other embodiments, the collector electrode 1024 can be a return electrode located elsewhere along the elongate body 1002, or it can be located on a second elongate body introduced into a patient's body.

In operation, the power supply and controller 1018 can drive the delivery of liquid into target tissue at a desired flow rate, the heating of the liquid to a desired therapeutic temperature, and the delivery of therapeutic ablative energy via the one or more ablation elements, such as electrode 1005. To do so, the power supply and controller 1018 can itself comprise a number of components for generating, regulating, and delivering required electrical control and therapeutic energy signals. For example, the power supply and controller 1018 can include one or more frequency generators to create one or more RF signals of a given amplitude and frequency. These signals can be amplified by one or more RF power amplifiers into relatively high-voltage, high-amperage signals, e.g., 50 volts at 1 amp. These RF signals can be delivered to the ablation element via one or more electrical connections 1022 and the elongate body 1002 such that RF energy is passed between the emitter electrode 1005 and the collector electrode 1024 that can be located remotely on a patient's body. In embodiments in which the elongate body is formed from non-conductive material, the one or more electrical connections 1022 can extend through the inner lumen of the elongate body or along its outer surface to deliver current to the emitter electrode 1005. The passage of RF energy between the ablation element and the collector electrode 1024 can heat the tissue surrounding the elongate body 1002 due to the inherent electrical resistivity of the tissue. The power supply and controller 1018 can also include a directional coupler to feed a portion of the one or more RF signals to, for example, a power monitor to permit adjustment of the RF signal power to a desired treatment level.

Note that the controller 1018 can also be configured to perform the methods described herein that permit monitoring of temperature in tissue remote from the elongate body or instrument. For example, the controller can be configured to deliver ablative energy and liquid for a first period of time and then to pause delivery of ablative energy and liquid. During the pause, the controller can detect a temperature of, e.g., the ablation element and/or temperature adjacent thereto and determine whether therapy should be terminated, resumed, or resumed with altered operating parameters based on a comparison of the detected temperature to a reference temperature. The controller 1018 can be automated to make various decisions based on desired safety margins, etc., or can be configured to communicate detected values and/or recommendations to a user via a user interface for direct user control.

The elongate body 1002 illustrated in FIG. 10 can be configured for insertion into a patient's body in a variety of manners. FIG. 11A illustrates one embodiment of a medical device 1100A having an elongate body 1102A disposed on a distal end thereof configured for laparoscopic or direct insertion into a target area of tissue. In addition to the elongate body 1102A, the device 1100A can include a handle 1104A to allow an operator to manipulate the device. The handle 1104A can include one or more electrical connections 1106A that connect various components of the elongate body (e.g., the heating assembly and ablation element 1105A) to, for example, the power supply and controller 1018 described above. The handle 1104A can also include at least one liquid conduit 1108A for connecting a liquid source to the device 1100A.

Figure 11B:
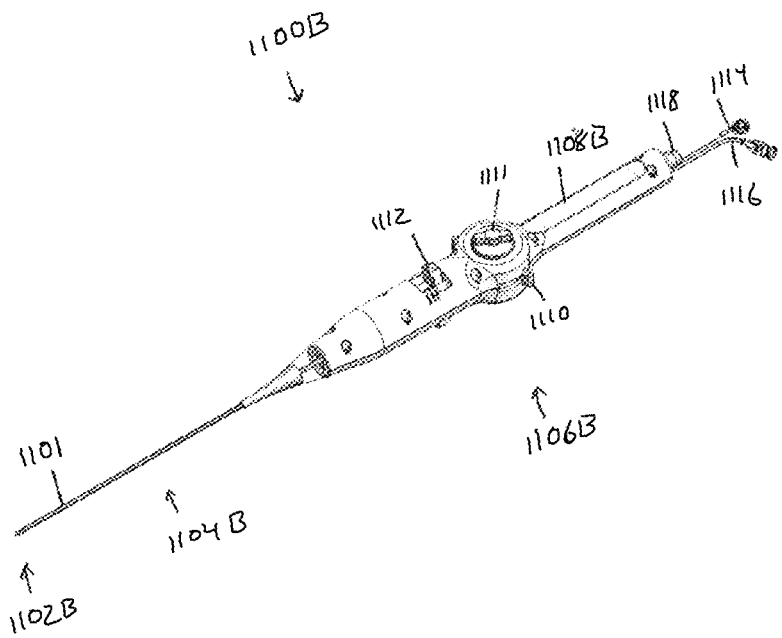

While device 1100A is one exemplary embodiment of a medical device that can be adapted for use in liquid enhanced ablation, a number of other devices can also be employed. For example, FIG. 11B illustrates an alternative embodiment of a catheter device 1100B configured for liquid enhanced ablation. While the devices and methods described herein can be used with any of a variety of surgical catheter devices, the device 1100B can be configured to deliver liquid enhanced ablation therapy to, for example, a patient's heart. The device 1100B generally includes a catheter 1101 having a distal portion 1102B and a flexible portion 1104B. A proximal portion 1106B of the device includes a handle 1108B, steering controls 1110, steering tension knob 1111, and advancing mechanism 1112 to control extension of an elongate body out of a distal end of the catheter 1101. Extending from a proximal end of the device are tubes 1114, 1116 that receive liquid for delivery during therapy and instrument flushing, respectively. An additional inlet 1118 at the proximal end of the device can receive any number of electrical power and control cables.

The device 1100B can have a variety of different sizes depending on its intended use. For example, in some embodiments the catheter 1101 can have a length of about 120 cm and a diameter of about 8 French, though any of a variety of other sizes can be utilized depending upon the intended application, treatment site, etc. The catheter can be formed from any of a variety of materials known in the art, including, for example, polyurethanes, nylons, and polyether amides, such as PEBAX®. The catheter 1101 can be flexible to allow for steering through tortuous pathways within the body using one or more steering cables, as described in more detail below.

Figure 12:
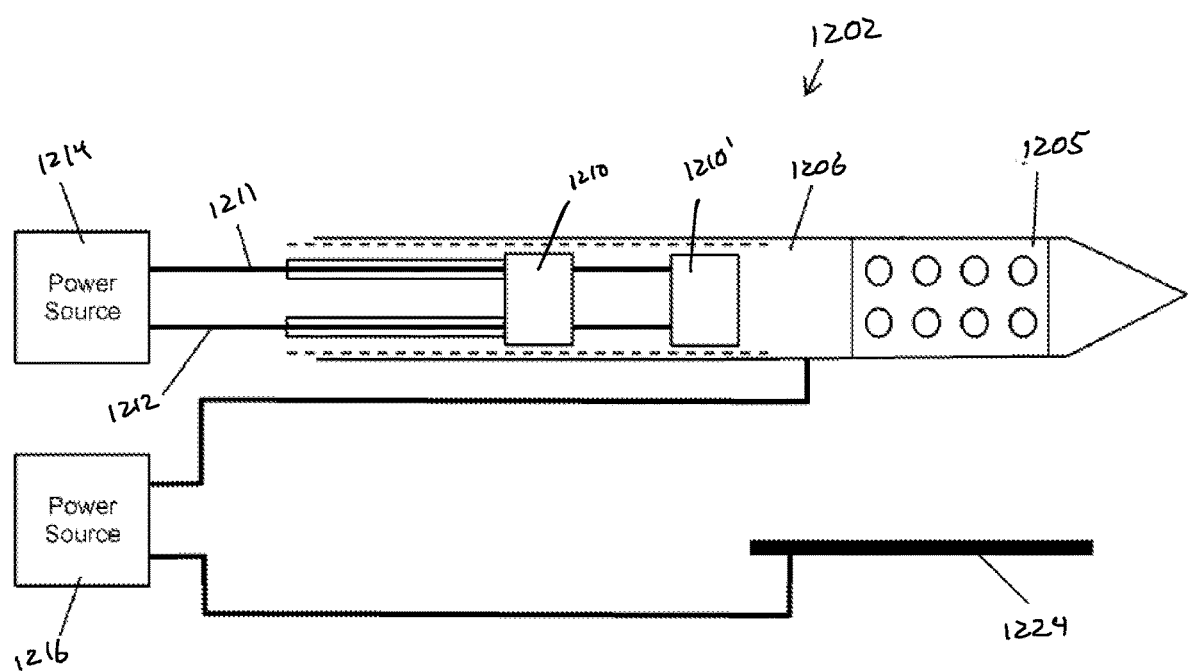
FIG. 12 is a diagram of one embodiment of an electrical circuit for driving an elongate body having a dual-wire heating assembly.
Figure 13:
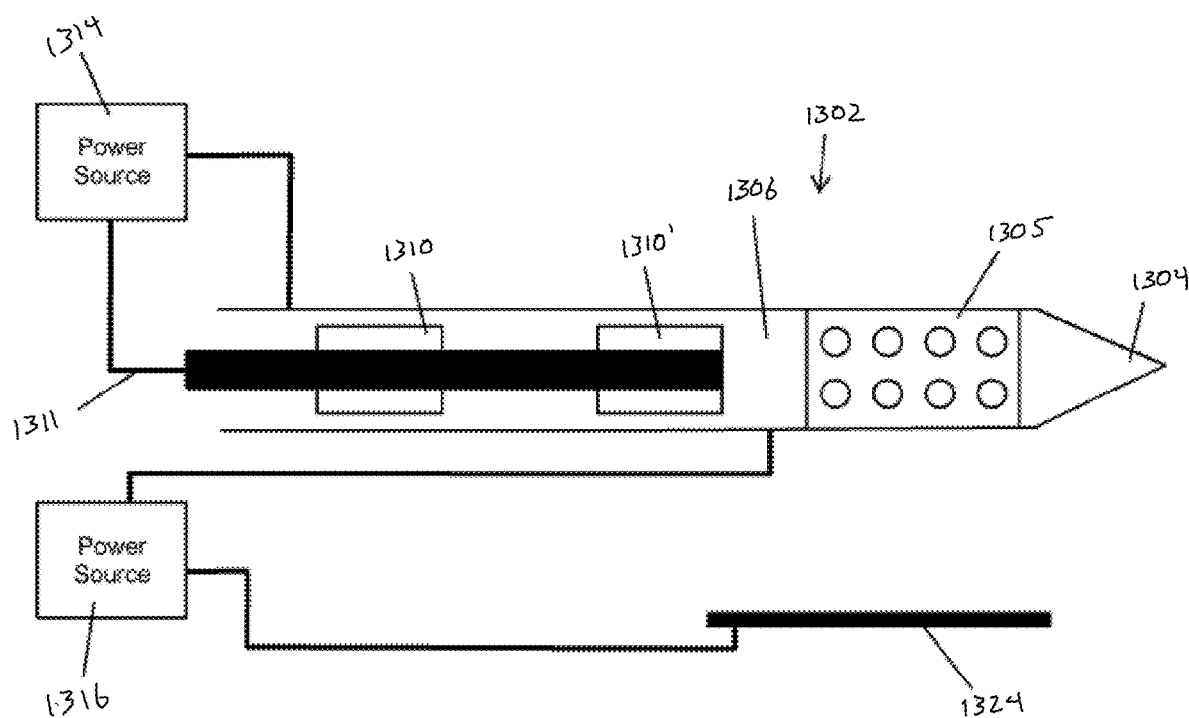
FIG. 13 is a diagram of one embodiment of an electrical circuit for driving an elongate body having a single-wire heating assembly.

FIGS. 12 and 13 illustrate exemplary embodiments of electrical circuits for delivering ablative energy, e.g., RF electrical energy, to tissue surrounding an elongate body 1202, 1302 and liquid flowing through inner lumens thereof. In the embodiment of FIG. 12, for example, two separate power sources 1214, 1216 are utilized to deliver electrical energy including, for example, RF energy. The power source 1214 can be connected to the two wires 1211, 1212 running through the inner lumen 1206 of the elongate body 1202. By passing electrical current through the wires, energy can be transmitted through the liquid flowing within the inner lumen 1206 between the exposed portions of the wires 1211, 1212.

The power source 1216 can be connected to both the elongate body 1202 and a collector electrode 1224. The collector electrode 1224 can be located remotely on a patient's body, for example, placed under a patient's back on an operating table. As discussed above, in other embodiments, the collector electrode 1224 can be co-located on the elongate body 1202 or it can be located on a second elongate body positioned nearby the elongate body 1202. Note that positioning the collector electrode 1224 on the elongate body 1202 requires isolating the emitter electrode 1205 from the collector electrode. This can be accomplished in a variety of manners including, for example, by forming the elongate body 1202 from a non-conducting material and placing the two electrodes on the surface of the elongate body 1202. In such an embodiment, the power source 1216 can be connected to the two electrodes by any suitable electrical connection, such as wires extending through the inner lumen of the elongate body 1202 or along its outer surface.

Referring back to the figure, the power source 1216 can deliver RF energy from the electrode 1205 to the collector electrode 1224 by passing electrical current through the elongate body 1202. The two power sources 1214, 1216 do not share a common electrical ground and therefore remain electrically isolated from one another. This ensures that power from the source 1214 heats only saline flowing within the elongate body 1202, while power from the source 1216 heats only tissue surrounding the elongate body 1202. Any of a variety of spacers 1210, 1210' and insulating materials can be utilized to prevent a short between the two wires 1211, 1212 that can result from the wires touching each other or simultaneously contacting the elongate body 1202.

FIG. 13 illustrates another embodiment of an electrical circuit for independently delivering RF energy to liquid flowing in an inner lumen 1306 of an elongate body 1302 having a distal tip 1304, as well as to tissue surrounding the elongate body. As shown in the figure, dual power sources 1314, 1316 can be used to deliver energy to the liquid within the inner lumen 1306 and the tissue surrounding the elongate body 1302, similar to the circuit illustrated in FIG. 12. However, in the illustrated embodiment, the circuits formed by each power source 1314, 1316 can share the elongate body 1302 as a common electrode. In other words, power source 1314, which is configured to deliver RF energy to liquid flowing within the inner lumen 1306, can be connected to the wire 1311 disposed within the inner lumen 1306 and to the elongate body 1302 itself. The elongate body 1302, then, can serve as an electrode for the power source 1314. In the illustrated embodiment, the wire 1311 can be prevented from contacting the elongate body 1302 by spacers 1310, 1310'. The power source 1316, on the other hand, can be connected to the elongate body 1302 and a collector electrode 1324. Accordingly, the power source 1316 can deliver RF energy from the electrode 1305 into tissue surrounding the elongate body 1302. As a result of the fact that the two power sources 1314, 1316 are only connected via the elongate body 1302 (i.e., only connected at a single point without a return connection), the power sources are able to operate independently and simultaneously without any current flowing therebetween.

Whether utilizing the above-described exemplary embodiments of liquid enhanced ablation therapy systems or some other form of irrigated ablation therapy, in some configurations compliance in the liquid delivery conduits and mechanisms of the system can interfere with measurement of temperature response during a pause in delivery of ablative energy and liquid. For example, pausing delivery of liquid (as in step 306 of the method shown in FIG. 3) can include stopping a pump configured to urge liquid toward a distal end of an ablation instrument (e.g., for introduction into tissue or recirculation within the instrument). The flow of liquid does not necessarily halt completely upon stopping the pump, however. This is because pressure from compliance in the pump itself and/or the liquid conduits that carry liquid from the pump to a distal end of the instrument can continue to cause liquid flow for a period of time. By way of further example, liquid pumps, including rotary impeller-driven pumps and linear syringe pumps, etc., can continue to move for a period of time following the halt of electrical current or other actuating or motivating force. In addition, pumps can include seals or other components that can be compressed during operation and will take some period of time to return to an uncompressed state after the pump is stopped. Moreover, liquid conduits typically have some degree of elasticity and can become distended during pump operation as a result of the increased pressure from liquid flow. Following pump stoppage, the liquid conduits can contract to their original state and this contraction can maintain liquid pressure and flow for a period of time.

This can have the practical effect of continuing liquid flow for some period of time even after the pause of delivery of ablative energy (e.g., step 306 of the method shown in FIG. 3). Continued liquid flow away from the ablation instrument during the pause in therapy can cause unintentional cooling of tissue in contact with the instrument, thereby delaying the heat transfer that causes the tissue in contact with the instrument to equalize with tissue more remotely located from the instrument. Given that the time of the pause can be short (e.g., less than a second in some embodiments, as described above), unintentional continued liquid flow due to system compliance can have a non-negligible effect.

To avoid unintentional continued liquid flow away from the ablation instrument after a pause in delivery of energy and liquid, in some embodiments a liquid pump can be reversed to create a negative pressure (e.g., suction) that counterbalances the pressure created by compliance in the system. For example, a syringe-type linear pump can be reversed a short distance to account for any compliance in the pump itself and/or the liquid conduits extending from the pump to the ablation instrument in order to ensure that liquid delivery is actually halted at the time of the desired pause in active therapy.

Moreover, in some embodiments utilizing an open loop instrument that delivers liquid into tissue surrounding an elongate body, the concept of halting liquid flow by reversing an actuating liquid pump can be extended to create suction that draws liquid from tissue immediately adjacent to the instrument back into the inner lumen of the elongate body. This can be accomplished, for example, by reversing an actuating pump by a greater degree than the above-described reversal solely to account for compliance in the ablation system components. Reversing liquid flow in this manner and drawing liquid from within adjacent tissue back into the inner lumen of the elongate body can accelerate the heat transfer that causes the ablation element (and any temperature sensor coupled thereto) to equalize with the temperature of surrounding tissue and thereby indicate whether more remote tissue is hotter, cooler, or the same temperature as tissue immediately adjacent to the elongate body. That is, by physically moving fluid from outside the inner lumen to inside the inner lumen, heat transfer by convection can be combined with conduction to more quickly bring a temperature sensor into equilibrium with surrounding tissue temperature.

Characterizing how much negative pressure is required to achieve either an instantaneous halt in the flow of liquid or a reversal in the flow of liquid will depend on the particular configuration of the system being used. For example, the length of liquid conduit used, the liquid conduit materials, the pressure and flow rate of liquid being delivered, the type of pump used, etc. can all influence the amount of system compliance. Further, reversing liquid flow may not be desirable in closed loop devices wherein the liquid is never introduced into the tissue and therefore cannot help transfer heat back toward the elongate body following a pause in active therapy. Further, drawing liquid from outside the instrument may also be undesirable in embodiments where an open loop device is disposed in, e.g., a liquid-filled body cavity (such as a blood vessel, etc.) rather than being disposed within a mass of tissue being treated. This is because the liquid surrounding the instrument in such an embodiment is likely to be equalized very quickly to the temperature of whatever liquid is flowing within the cavity and not necessarily to the temperature of the tissue that the instrument is in contact with (e.g., a wall of the cavity). In closed loop devices or open loop devices in a cavity or tissue, however, accounting for system compliance to cause a timely pause in the internal flow of liquid can be desirable, as continued liquid flow can cool the ablation element and depress any possible detected increase in temperature.

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A method for ablating tissue, comprising:
positioning an elongate body proximate to the tissue, the elongate body having an ablation element and at least one temperature sensor coupled thereto;
simultaneously delivering an ablative energy to the tissue through the ablation element and a liquid flow to the tissue through the elongate body;
pausing delivery of the ablative energy to the tissue and pausing delivery of the liquid flow to the tissue;
creating a negative pressure in response to pausing delivery of the ablative energy and the liquid flow to the tissue;
sensing a temperature of the ablation element while delivery of the ablative energy and the liquid flow to tissue is paused; and
any of terminating delivery of the ablative energy and liquid flow to the tissue, and resuming delivery of the ablative energy and the liquid flow to the tissue based on a comparison of the sensed temperature to a reference temperature.

2. The method of claim 1, wherein positioning the elongate body proximate to the tissue includes inserting the elongate body into a tissue mass comprising the tissue.

3. The method of claim 2, wherein delivering the liquid flow to the tissue comprises delivering the liquid flow through at least one outlet port formed in the elongate body.

4. The method of claim 1, wherein positioning the elongate body proximate to the tissue includes contacting the tissue with a distal portion of the elongate body without penetrating the tissue.

5. The method of claim 4, wherein the liquid flow delivered to the tissue through the elongate body is released through at least one outlet port formed in the elongate body.

6. The method of claim 4, wherein the liquid flow delivered to the tissue through the elongate body is recirculated without exiting the elongate body.

7. The method of claim 1, wherein the delivery of the ablative energy and the liquid flow to the tissue is terminated if the sensed temperature is greater than the reference temperature.

8. The method of claim 7, wherein the delivery of the ablative energy and the liquid flow to the tissue is terminated if a difference between the sensed temperature and the reference temperature is greater than a threshold amount.

9. The method of claim 1, wherein the delivery of the ablative energy and the liquid flow to the tissue is resumed if the sensed temperature and the reference temperature are substantially equal.

10. The method of claim 1, wherein resuming the delivery of the ablative energy and the liquid flow to the tissue further comprises adjusting at least one of a power level of the ablative energy, a temperature of the liquid, or a flow rate of the liquid.

11. The method of claim 10, wherein at least one of the power level of the ablative energy or the temperature of the liquid is decreased if the sensed temperature is greater than the reference temperature.

12. The method of claim 10, wherein at least one of the power level of the ablative energy or the temperature of the liquid is increased if the sensed temperature is less than the reference temperature.

13. The method of claim 10, wherein the flow rate of the liquid is increased if the sensed temperature is greater than the reference temperature.

14. The method of claim 10, wherein the flow rate of the liquid is decreased if the sensed temperature is less than the reference temperature.

15. The method of claim 1, wherein the delivery of the ablative energy and the liquid flow to the tissue is paused for about 10 seconds.

16. The method of claim 1, wherein pausing the delivery of the ablative energy and the liquid flow to the tissue occurs after about 15 seconds of simultaneously delivering the ablative energy and the liquid flow to the tissue.

17. The method of claim 1, further comprising heating the liquid within the elongate body.

18. The method of claim 17, wherein the liquid is heated to a temperature of about 40° C. to about 80° C.

19. The method of claim 1, wherein a flow rate of the liquid is up to about 20 ml/min.

20. The method of claim 1, wherein the ablation element is an electrode and the ablative energy is electrical energy.

21. The method of claim 1, further comprising drawing the liquid from outside the elongate body into the elongate body after pausing the delivery of the ablative energy and the liquid flow to the tissue.

22. The method of claim 1, wherein delivering the liquid flow to the tissue through the elongate body is accomplished using a pump and creating a negative pressure to pause delivery of the liquid flow to the tissue includes reversing the pump.

23. The method of claim 1, wherein creating the negative pressure further comprises drawing liquid from the tissue immediately adjacent to the elongate body back into the elongate body.

* * * * *